United States Patent [19]
Fisher

[11] Patent Number: 6,054,568
[45] Date of Patent: Apr. 25, 2000

[54] NUCLEOBASE OLIGOMERS

[75] Inventor: Peter V. Fisher, El Granada, Calif.

[73] Assignee: The Perkin-Elmer Corporation, Foster City, Calif.

[21] Appl. No.: 09/008,805

[22] Filed: Jan. 16, 1998

[51] Int. Cl.[7] .......................... C07H 19/00; C07H 21/02; C07H 21/01; C12Q 1/68
[52] U.S. Cl. .......................... 536/23.1; 435/6; 435/91.1; 435/91.2; 536/22.1; 536/25.3; 536/25.32; 536/25.33; 536/25.34
[58] Field of Search ............................. 435/6, 91.1, 91.2; 536/22.1, 23.1, 25.3, 25.32, 25.33, 25.34

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,931,223 | 6/1990 | Bronstein et al. | 252/700 |
| 4,962,192 | 10/1990 | Schaap | 536/18.1 |

OTHER PUBLICATIONS

Uhlman et al. "Antisense Oligonucleotides: A New Therapeutic Principle" Chemical Reviews vol. 90, No. 4 pp. 543–584, Jun. 1990.

Andrus, Alex, "Chemical methods for 5' non–isotopic labelling of PCR probes and primers," *PCR2: A Practical Approach*, Oxford University Press, Oxford, pp. 39–54 (1995).

Beaucage et al., "Advances in the Synthesis of Oligonucleotides by the Phosphoramidite Approach," *Tetrahedron* 48(12):2223–2311 (1992).

Beaucage et al., "The Functionalization of Oligonucleotides Via Phosphoramidite Derivatives," *Tetrahedron* 49(10):1925–1963 (1993).

Beaucage et al., "The Synthesis of Modified Oligonucleotides by the Phosphoramidite approach and Their Applications," *Tetrahedron* 49(28):6123–6194 (1993).

Beaucage et al., "The Synthesis of Specific Ribonucleotides and Unrelated Phosphorylated Biomolecules by the Phosphoramidite Method," *Tetrahedron* 49(46):10441–10488 (1993).

Blackburn et al., "DNA and RNA Structure," *Nucleic acids in chemistry and biology*, Chapt. 2, Second Edition, Oxford University Press, Oxford, pp. 15–22 (1996).

Blackburn et al., "DNA and RNA Structure," *Nucleic acids in chemistry and biology*, Chapt. 2, Second edition, Oxford University Press, Oxford, pp. 70–71 (1996).

Breslauer et al., "Predicting DNA duplex stability from the base sequence," *Proc. Natl. Acad. Sci. USA* 83:3746–3750 (Jun. 1986).

Bronstein et al., "1,2–Dioxetanes: Novel Chemiluminescent Enzyme Substrates. Applications to Immunoassays," *J. Biolumin. Chemilumin.* 4:99–111 (1989).

Froehler et al., "Oligodeoxynucleotides Containing C–5 Propyne Analogs of 2'–Deoxyuridine and 2'–Deoxycytidine," *Tetrahedron Letters* 33(37):5307–5310 (1992).

(List continued on next page.)

*Primary Examiner*—Jezia Riley
*Attorney, Agent, or Firm*—Alex Andrus

[57] ABSTRACT

A novel class of compounds, exemplified by oligomers comprised of purine, pyrimidine, and other nucleobase monomers are disclosed. The nucleobase oligomers hydrogen bond through Watson/Crick base pairing to complementary nucleic acids, such as DNA and RNA, in an opposing strand. Each internal nucleobases in the oligomer has two attachment sites and is attached to two nucleobases by linkers. Terminating groups may contain reactive functionality, labels, reporters, or nucleic acids. The nucleobase oligomer compounds are useful as sequence specific recognition molecules for complementary nucleic acids. Where the molecule consists of sections of nucleobase oligomer and nucleic acid, the chimera may be an enzyme substrate in cleavage, ligation, and primer extension methods such as PCR and DNA sequencing.

15 Claims, 16 Drawing Sheets

OTHER PUBLICATIONS

Hermanson, Greg T., *Bioconjugate Techniques,* Chapt. 3, Academic Press, San Diego, pp. 40–56 (1996).

Kricka, Larry J., Ed., *Nonisotopic DNA Probe Techniques,* Chapt. 1, Academic Press, San Diego, pp. 3–28 (1992).

Nielsen et. al., "Sequence–Selective Recognition of DNA by Strand Displacement with a Thymine–Substituted Polyamide," *Science* 254:1497–1500 (Dec. 1991).

Saiki et al., "Primer–Directed Enzymatic Amplification of DNA with a Thermostable DNA Polymerase," *Science* 239:487–491 (Jan. 1988).

Sanger et al., "DNA sequencing with chain–terminating inhibitors," *Proc. Natl. Acad. Sci. USA* 74(12):5463–5467 (Dec. 1977).

Seela et al., "Oligonucleotides Containing Consecutive 2'–Deoxyisoguanosine Residues: Synthesis, Duplexes with Parallel Chain Orientation, and Aggregation," *Helv. Chim. Acta* 80:73–85 (1997).

Stryer, Lubert, "Fluorescence Energy Transfer as a Spectroscopic Ruler," *Ann. Rev. Biochem.* 47:819–846 (1978).

N-1, C-5 uracil

N-1, C-6 cytosine

N-9, C-8 guanine

N-9, C-7 7-deaza-adenine

C-5, N-1 cytosine

C-6, N-1 cytosine

C-6, N-1 thymine

C-5, N-1 uridine

C-5, N-1 5,6-dihydrouridine

C-6, N-1 5,6-dihydrothymine

C-6, N-1 C-5-propynyl uridine

C-5, N-1 C-5-propynyl uridine

C-6, N-1 C-5-propynyl cytosine

C-5, N-1 C-5-propynyl cytosine

C-8, N-9 adenineC-7, N-9 7-deaza-adenineC-8, N-9 guanine

C-7, N-9 7-deaza-guanineC-8, N-9 7-deaza-adenineC-8, N-9 7-deaza-guanine

C-8, N-9 2-thio-guanineC-7, N-9 2-thio-7-deaza-guanineC-8, N-9 2,6-diaminopurine C-7, N-9 7-deaza-2,6-diaminopurineC-8, N-9 isoguanineC-7, N-9 7-deaza-isoguanine

NUCLEOBASE OLIGOMERS

BACKGROUND

Many nucleic acid analogs of DNA and RNA have been synthesized and shown to have markedly different molecular recognition properties. The central feature of molecular recognition by well-ordered, intermolecular hydrogen-bonding between linear strands of nucleic acids (Blackburn, G. M. and Gait, M. J. Eds. "DNA and RNA structure" in *Nucleic Acids in Chemistry and Biology*, $2^{nd}$ Edition, (1996) Oxford University Press, p. 15–22), can be grossly affected by structural modifications. Some analogs have greater affinity for their complementary DNA and RNA, exemplified by higher thermal melting values, $T_m$. In this effect, affinity is synonymous with hybridization strength and duplex stability. Ideally, nucleic acid analogs demonstrate a high degree of base-discrimination following the normal Watson/Crick rules (A+T, G+C). The level of discrimination, or specificity, is best measured in experiments that compare the $T_m$ values of duplexes having perfect Watson/Crick complementarity versus those with one or more mismatches (e.g. A+G or A+C). The destabilization, seen by the decrease in $T_m$, is a measure of specificity, pertinent to structural modifications, hybridization conditions, or other experimental parameters. Although some nucleic acid analogs have superior properties, most show impaired and deficient thermal melting values.

Additionally, some nucleic acids and analogs can form higher order structures than duplexes. For example, triplex structures involve three strands bound in a sequence dependent manner. While higher order structures exist in nature and play important roles in gene expression, recombination, and replication, they can lessen or complicate the intended, targeted activity of an exogenous nucleic acid analog. Therefore, it is desirable for most purposes that nucleic acid analogs have clear and predictable molecular recognition properties. The most desirable molecular recognition properties of a nucleic acid analog are high affinity and specificity in Watson/Crick base-pairing.

Exogenous nucleic acids outside the cell nucleus and replicative organelles are rapidly degraded and metabolized by enzymes. Structural analogs of nucleic acids often are poor substrates for phosphodiesterase, exo- and endonucleases which rapidly degrade foreign DNA and RNA. Thus, nuclease-resistant analogs attain a higher, more stable intracellular concentration and can exert their antisense, and other hybridization-dependent effects, over a useful period of time in vitro or in vivo. It is desirable that nucleic acid analogs be nuclease-resistant.

Although many nucleic acid analogs have some desirable properties, such analogs may have numerous other properties that render them unsuitable for common molecular biology techniques such as PCR or nucleic acid sequencing. For example, peptide nucleic acids—PNA (Nielsen, P. E. etal, *Science* (1991) 254:1497–1500) cannot function as primer extension templates or primers because they are not substrates for ligase, polymerase, or restriction enzymes. Accordingly, it is of interest to provide nucleic acid analogs that have such useful properties. It is also of interest to provide nucleic acid analogs that have one or more properties that are advantageous with respect to corresponding DNA molecules, but may also be used in a variety of molecular biology methods including annealing, ligation, sequencing, cleavage, PCR, and other primer extension reactions. It is of further interest to provide methods of using such analogs.

SUMMARY

The present invention is directed toward a class of novel nucleobase oligomers useful for sequence-specific molecular recognition of complementary nucleic acids and uses for the novel nucleobase oligomers.

It is an object of certain embodiments of the present invention to provide nucleobase oligomers having increased intramolecular and intermolecular duplex stability as compared with natural nucleic acids, such as DNA and RNA, and nucleic acid analogs.

It is another object of certain embodiments of the present invention to provide nucleobase oligomers having heteroduplex structures that induce A-type or B-type helix formation when a strand of nucleobase oligomer is base-paired with a strand of nucleic acid such as DNA or RNA (FIGS. 4–7 for example).

It is yet another object of certain embodiments of the present invention to provide nucleobase oligomers having increased resistance to nuclease degradation as compared with natural nucleic acids.

It is an additional object of certain embodiments of the present invention to provide nuclcobase oligomers having increased chemical stability as compared with known nucleic acids.

It is another object of certain embodiments of the present invention to provide nucleobase oligomers having an increased rate of transport into a living cell as compared with known nucleic acids.

It is yet another object of certain embodiments of the present invention to provide nucleobase oligomers which provide signaling, labeling, covalent attachment, capture derivatization, and detection capability.

It is an additional object of certain embodiments of the present invention to provide chimeras, comprising nucleobase oligomers and nucleic acids, and having one or more of the properties described above. The chimeras comprise nucleobase monomers and nucleotide monomers in any ratio, sequence order, or sequence composition. In a preferred embodiment of the invention, the chimeras consist of a section of nucleobase monomers and a section of nucleotide monomers wherein the 5' termini of the nucleotide section is attached to the nucleobase section and the nucleotide section bears a 3' hydroxyl. Such chimeras may be useful substrates for polymerase enzymes in primer extension reactions.

Embodiments of the nucleobase oligomers (or chimeras thereof) of the invention have a repeating polymer structure of purine, pyrimidine or analog nucleobases with two attachment sites on each nucleobase of the polymer. In one embodiment, the nucleobases may be selected from the group consisting of 7-deaza-adenine, 7-deaza-guanine, adenine, guanine, cytosine, thymine, and uracil, wherein the attachment sites are carbon or nitrogen atoms. In a preferred embodiment, the attachment sites are at N-1 and either C-5 or C-6 of pyrimidines and analogs and at N-9 and C-8 or C-7-deaza of purines and analogs (FIGS. 1A–1D). One or more nucleobases may be substituted at a third site, not attached to another nucleobase or terminating group, X or Y, with reactive functionality, detection labels, and capture labels. The attachment sites are bridged by linkers. Suitable linkers include alkylene, substituted alkylene, substituted aryl, neutral and anionic phosphorus groups, disulfide, amide, ester, carbonyl, sulfonamide, carbamate, urea, ethyleneoxy and polyethyleneoxy. In a preferred embodiment, the linker is an amide group or a phosphodiester group. In a particularly preferred embodiment, the linker is a phosphodiester group. The termini of the nucleobase oligomers may include terminating groups, such as hydrogen, substituted alkyl, substituted aryl, heteroatom groups, reactive functionality, detection labels, capture labels, and nucleic acids. In a preferred embodiment, the termini include fluorescent dyes, chemiluminescent precursors, biotin, hydroxymethyl, aminomethyl, mercaptomethyl, and carboxymethyl. In a particularly preferred embodiment, the termini include nucleic acids selected from the group consisting of DNA, RNA, and other nucleic acid analogs with internucleotide, sugar, or nucleobase modifications.

In addition to providing various novel nucleobase oligomers, the invention also includes the monomer subunits that may be used to synthesize the subject nucleobase oligomers. Furthermore, the invention includes methods of synthezing the subject nucleobase oligomers.

BRIEF DESCRIPTION OF THE DRAWINGS

Generally, the nucleobase oligomers and chimeras thereof of the invention are linear polymers. Illustrations of preferred embodiments are shown in the Figures. These illustrations are not intended to denote optimum length or sequence composition, or to exhaust the possible structures. The illustrations shown are not intended to restrict the scope of the invention.

DEFINITIONS

Unless stated otherwise, the following terms and phrases as used herein are intended to have the following meanings:

"Nucleic acids" are DNA and RNA biopolymers that encode, store, replicate, and express the total genetic information of an organism. Nucleic acids, like other biopolymers such as proteins, peptides, and polysaccharides, are composed of repeating monomeric units, i.e. nucleotides.

As used herein, the terms "polynucleotide" or "oligonucleotide" refer to linear polymers of natural nucleotide monomers or analogs thereof, including double and single stranded deoxyribonucleotides "DNA", ribonucleotides "RNA", α-anomeric forms thereof, and the like. In other words, an "oligonucleotide" is a chain of deoxyribonucleotides or ribonucleotides, that are the structural units that comprise deoxyribonucleic acid (DNA) and ribonucleic acid (RNA), respectively.

The term "nucleotide" is the monomer unit in biopolymer nucleic acids, such as DNA or RNA. A nucleotide is composed of three moieties: sugar, phosphate, and nucleobase. When part of a duplex, nucleotides are also referred to as "bases" or "base pairs".

The term "nucleoside" refers to a nucleotide that lacks a phosphate moiety. Usually the nucleoside monomers are linked by phosphodiester linkages, where as used herein, the term "phosphodiester linkage" refers to phosphodiester bonds or bonds including phosphate analogs thereof, including associated counter-ions, e.g., $H^+$, $NH_4^+$, $Na^+$, and the like. Polynucleotides typically range in size from a few monomeric units, e.g. 8–40, to several thousand monomeric units. Most molecular biology applications for polynucleotides require unique sequences of 15–30 nucleotides in length. Whenever a DNA polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted.

The terms "Watson/Crick base-pairing" and "Watson/Crick complementarity" refer to the pattern of specific pairs of nucleotides, and analogs thereof, that bind together through hydrogen-bonds, e.g. adenine (A) pairs with thymine (T), and guanine (G) pairs with cytosine (C).

The term "nucleobase" refers to the part of a nucleotide that bears the Watson/Crick base-pairing functionality. FIG. 1 shows the conventional nucleobase numbering scheme. The most common naturally-occurring nucleobases, adenine (A), guanine (G), uracil (U), cytosine (C, and thymine (T) bear the hydrogen-bonding functionality that binds one nucleic acid strand to another in a sequence specific manner.

"Nucleic acid analogs" are also polymeric, or "oligomeric", in composition, made by chemical synthesis from monomeric nucleotide analog units, and possess some of the qualities and properties associated with nucleic acids.

Figure 1A:
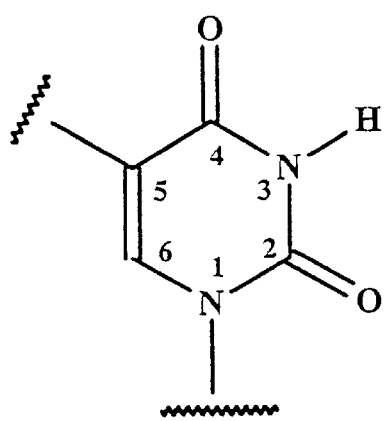
FIGS. 1A–1D Nucleobase position numbering of examples: 1A. N-1, C-5 uracil; 1B. N-1, C-6 cytosine; 1C. N-9, C-8 guanine; 1D. N-9, C-7-deaza-adenine.
Figure 1B:
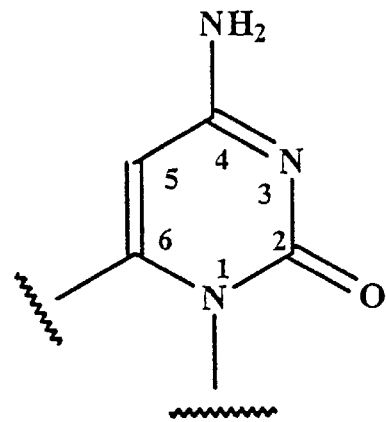
Figure 1C:
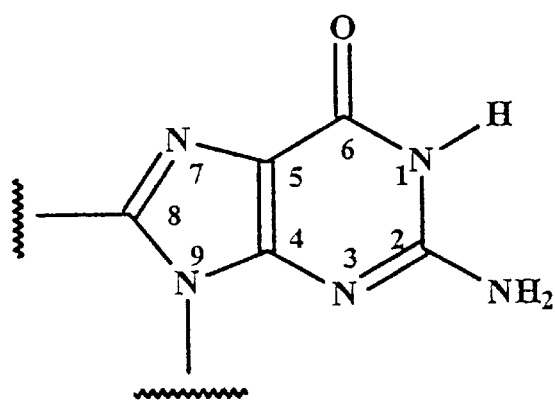
Figure 1D:
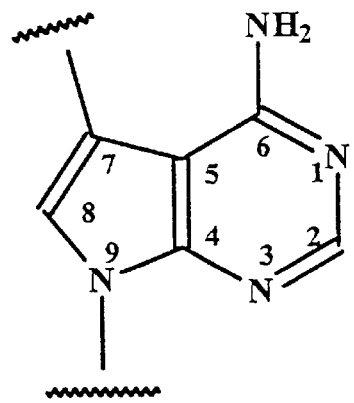
Figure 2:
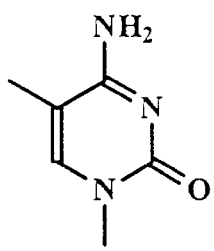
FIG. 2 Pyrimidine nucleobase examples.
Figure 2:
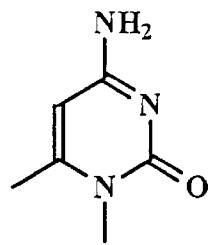
Figure 2:
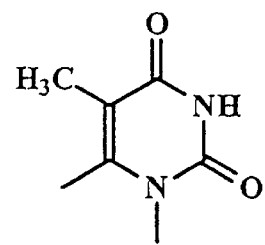
Figure 2:
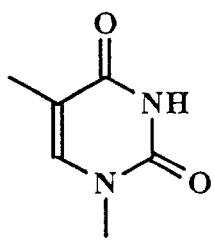
Figure 2:
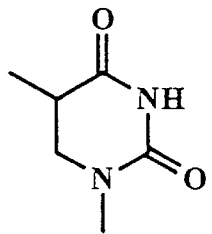
Figure 2:
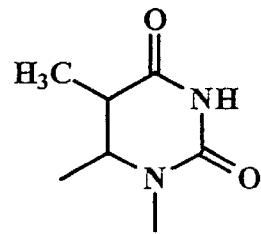
Figure 2:
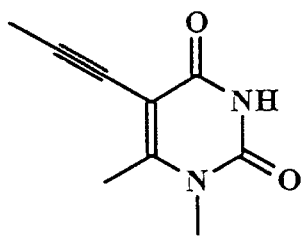
Figure 2:
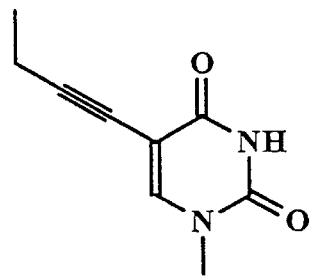
Figure 2:
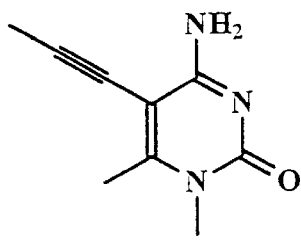
Figure 2:
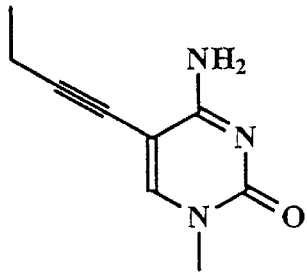
Figure 3:
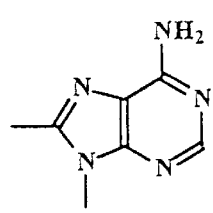
FIG. 3 Purine nucleobase examples.
Figure 3:
Figure 3:
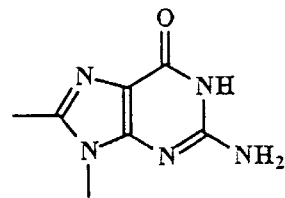
Figure 3:
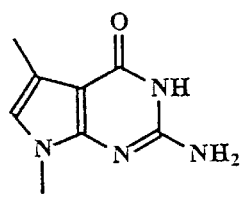
Figure 3:
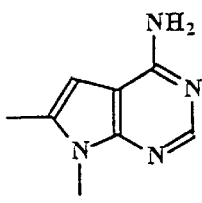
Figure 3:
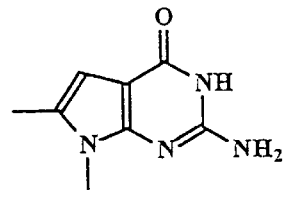
Figure 3:
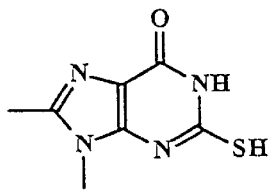
Figure 3:
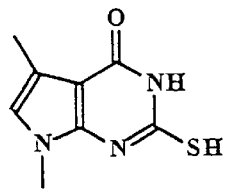
Figure 3:
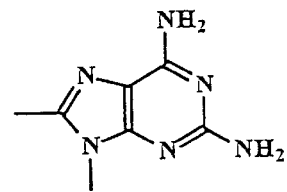
Figure 3:
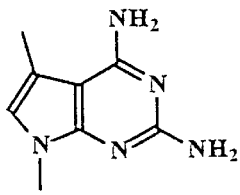
Figure 3:
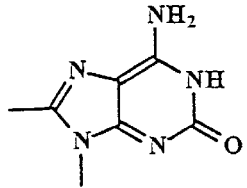
Figure 3:
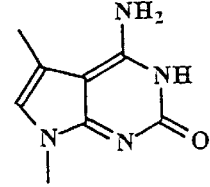
Figure 4:
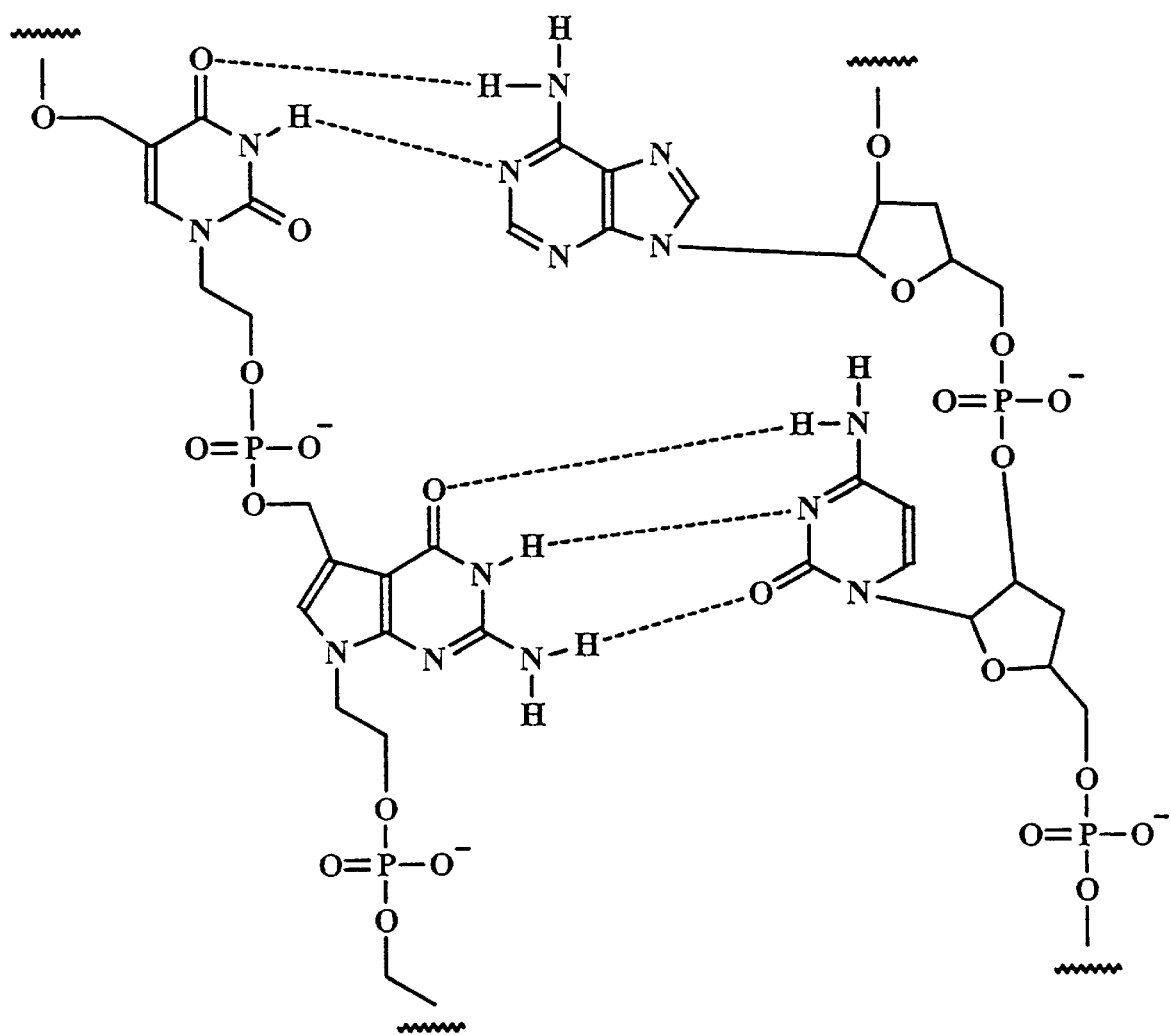
FIG. 4 Watson/Crick base-pairing of C-5-methyl, N-1-ethyl phosphodiester uracil, C-7-methyl, N-9-ethyl phosphodiester 7-deaza-guanine nucleobase oligomer to adenine and cytidine of deoxyribonucleic acid.
Figure 5:
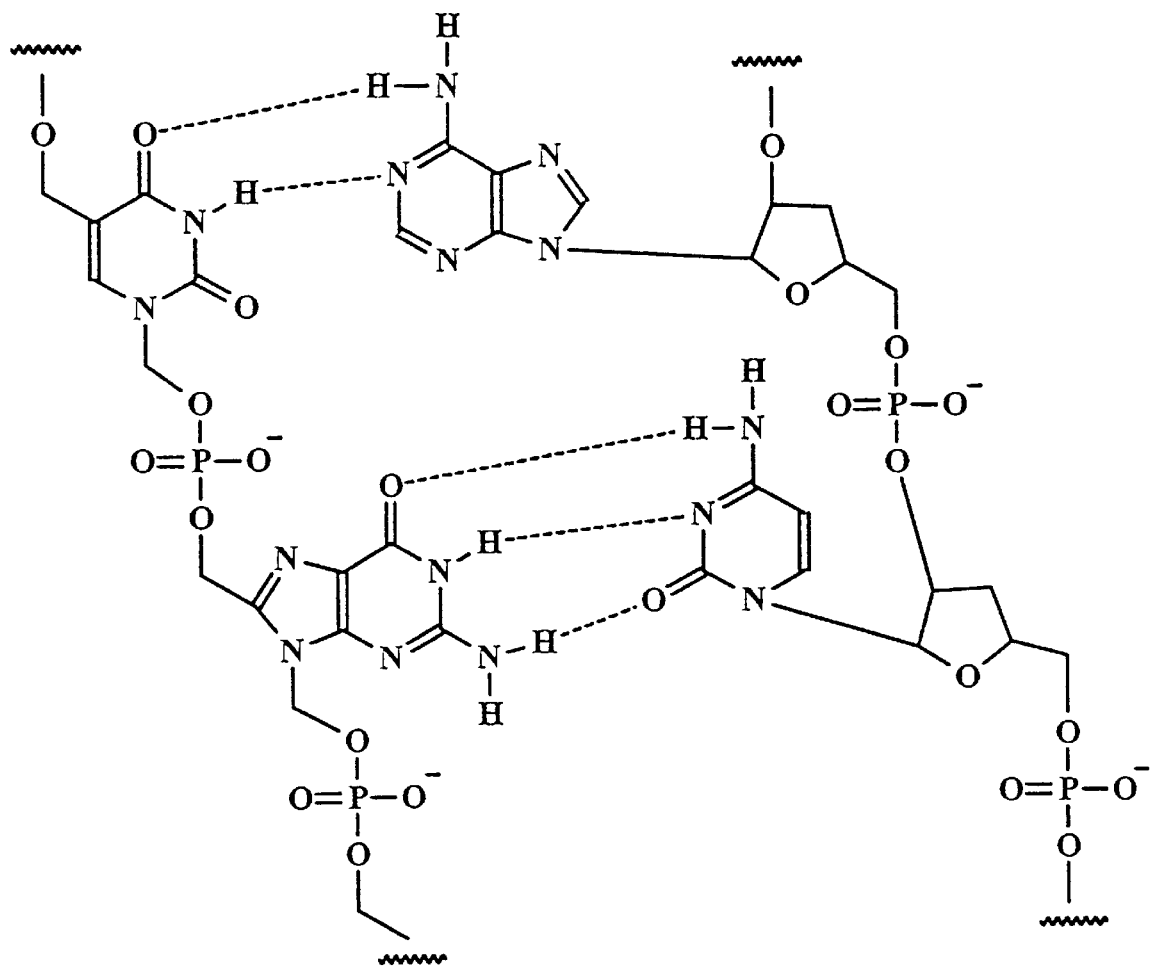
FIG. 5 Watson/Crick base-pairing of C-5-methyl, N-1-methyl phosphodiester uracil, C-8-methyl, N-9-methyl phosphodiester guanine nucleobase oligomer to adenine and cytidine of deoxyribonucleic acid.
Figure 6:
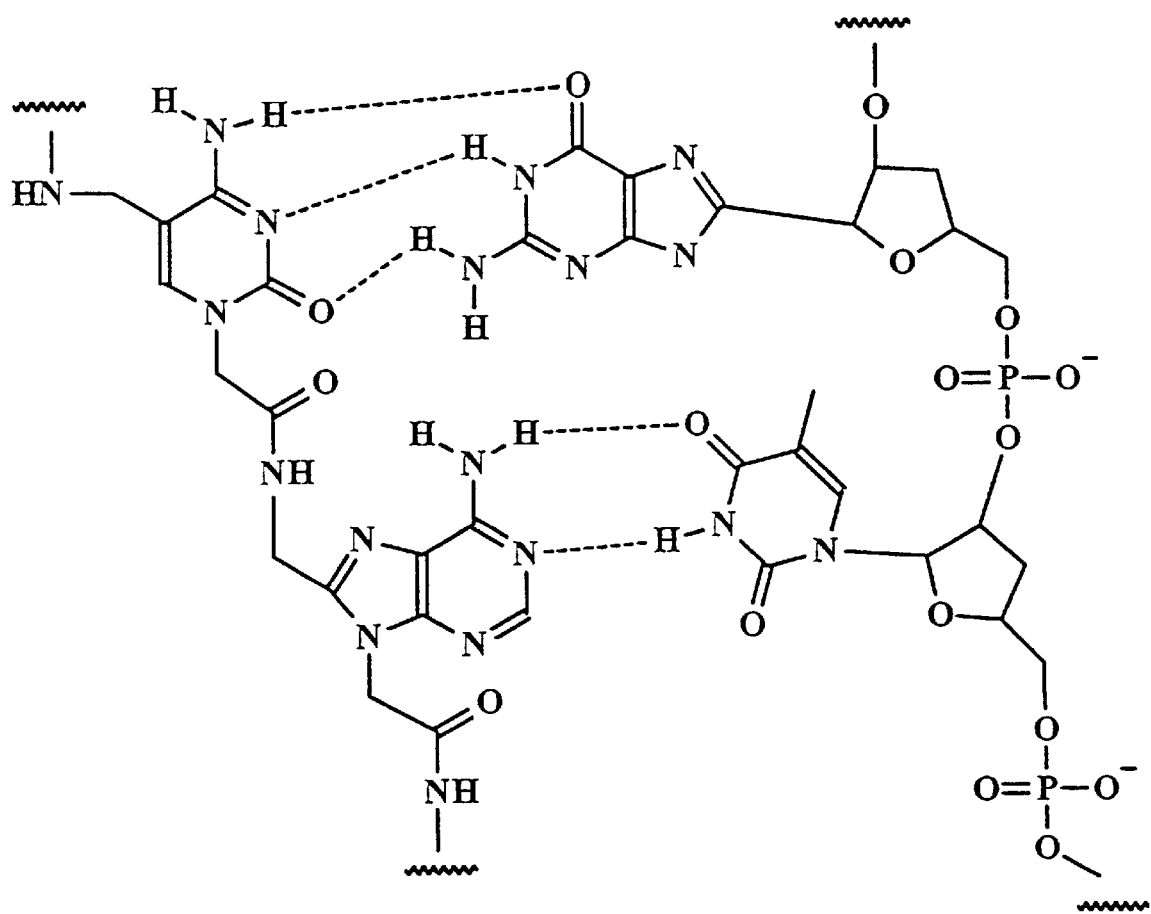
FIG. 6 Watson/Crick base pairing of C-5-methyl, N-1-methyl amide cytosine, C-8-methyl, N-9 methyl amide adenine nucleobase oligomer to guanine and thymine of deoxyribonucleic acid.
Figure 7:
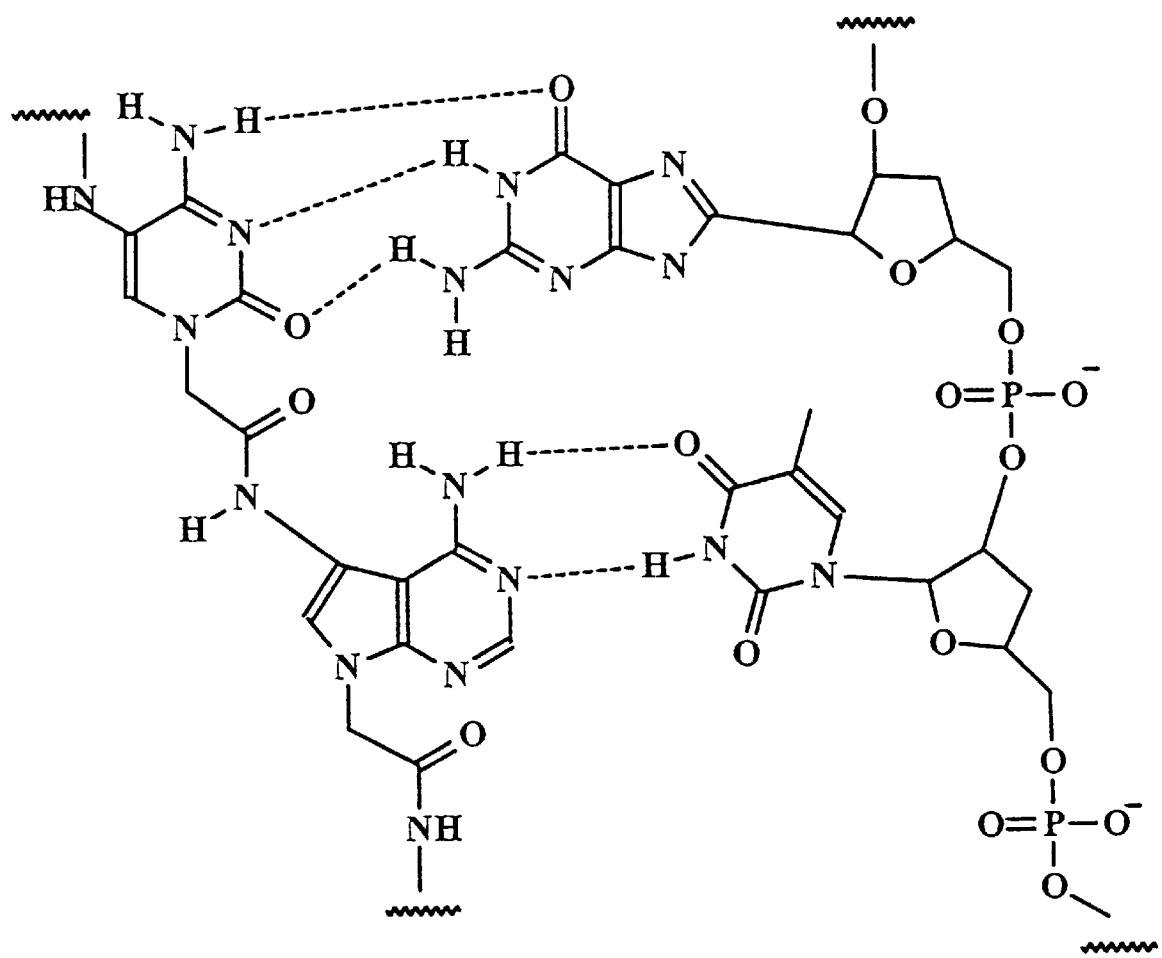
FIG. 7 Watson/Crick base pairing of C-5, N-1-methyl amide cytosine, C-7, N-9-methyl amide adenine to guanine and thymine of deoxyribonucleic acid.

"Nucleobase oligomer" refers to a polymer comprising the "nucleobase" moiety of nucleotides as the monomeric unit wherein each of the constituent nucleobase monomers has two attachment sites. Each nucleobase monomer is attached to two nucleobase monomers except at the termini. FIGS. 2 and 3 shows examples of some of the preferred pyrimidine and purine nucleobases, respectively.

The term "attachment site" refers to the atom on the ring system of a nucleobase to which is attached the linker that connects said nucleobase to an adjacent nucleobase.

The term "linker" refers to one or more atoms comprising a chain connecting nucleobases and terminating groups.

The term "terminating group" refers to one or more atoms located at the termini of the nucleobase oligomer. Terminating groups may possess functionality for chemical reactions to join other molecules or to effect changes in other molecules. Terminating groups may include capture labels, detection labels, and nucleic acids, including nucleic acid analogs.

The term "chimera" as used herein refers to an oligonucleotide including one or more nucleobase oligomer monomer units, and also including either DNA or RNA nucleotides.

The term "phosphodiester analog" refers to analogs of natural phosphodiester 3',5'-internucleotide linkages differing in their composition and/or location of attachment to a nucleotide, including but not limited to 2',5'-linkage, 3',3'-linkage, 5',5'-linkage, methyl phosphonate, alkylated phosphotriester, 3'-N-phosphoramidate, and PNA.

The term "lower alkyl", "lower alkylene" and "lower substituted alkylene" refers to straight-chain, branched, or cyclic groups consisting of 1–12 carbon atoms.

The term "label" refers to a group covalently attached at one or both termini of the nucleobase oligomer. The label is capable of conducting a function such as giving a signal for detection of the molecule by such means as fluorescence, chemiluminescence, and electrochemical luminescence. (Kricka, L. "Nonisotopic DNA Probe Techniques" (1992), Academic Press, San Diego, pp. 3–28). Alternatively, the label allows for separation or immobilization of the molecule by a specific or non-specific capture method (Andrus, A., "Chemical methods for 5' non-isotopic labelling of PCR probes and primers" in *PCR 2: A Practical Approach*, (1995), Oxford University Press, Oxford, pp. 39–54).

The term "chemiluminescent" refers to the light or photon generating capability of a compound. Typically chemiluminescence is initiated upon an event, such as cleavage of a bond which generates an unstable intermediate that fragments and releases light or a photon as part of the high-energy state decay process (Bronstein, I., Edwards, B. and Voyta, J. *J. Biolumin. Chemilumin.* (1989) 4:99–111; U.S. Pat. Nos. 4,931,223; 4,962,192).

The term "detection" refers to detecting, observing, or measuring a nucleobase oligomer on the basis of the properties of a covalently-attached detection label. Detection labels include, but are not limited to, fluorescent dyes, such as fluorescein and rhodamine derivatives, cyanine dyes, and energy-transfer dyes (Stryer, L. *Annu. Rev. Biochem.* (1978) 47:819–46).

The term "capture" refers to capturing, immobilizing, separating, or sequestering a nucleobase oligomer on the basis of the properties of a capture label covalently attached to the nucleobase oligomer. Capture labels include, but are not limited to, biotin, digoxigenin, fluorescein, 2,4-dinitrophenyl, and hydrophobic modifiers such as cholesterol, trityl and trityl derivatives, polyethylene glycol, poly-lysine, triglycerides, and high-molecular weight hydrocarbons.

The term "primer" refers to an oligonucleotide capable of selectively annealing to a specified target nucleic acid and thereafter serving as a point of initiation of a primer extension reaction wherein the primer is extended in a 5'→3' direction.

"Primer extension reaction" refers to a reaction between a target/primer duplex and a nucleotide which results in the addition of the nucleotide to a 3'-end of the primer such that the added nucleotide is complementary to the corresponding nucleotide of the target nucleic acid.

DETAILED DESCRIPTION

The invention relates to nucleobase oligomer compounds having the structure:

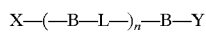

B is a nucleobase with Watson/Crick base-pairing properties bearing two linking attachment sites; at N-1 and either C-5 or C-6 of pyrimidines and analogs, and at N-9 and C-8 or C-7-deaza of purines and analogs. Examples of nucleobase attachment sites are shown in FIG. 1. The nucleobase units, B, in the nucleobase oligomers of the present invention may be purine or pyrimidine bases. Such bases may be purines adenine (A), guanine (G) and hypoxanthine (H), or of the pyrimidines uracil (U), cytosine (C), or thymine (T). B may also be other nucleobases. When reference is made herein to the use of purine or pyrimidine bases, such expressions are intended to include analogs of such bases. Analogs of pyrimidine and purine bases include amino-, aza- or deaza- and iso-analogs and the like (FIGS. 2 and 3). Alternatively, any other nucleobase isolated from natural sources may be used. Many different nucleobase sequences are possible in a nucleobase oligomer. L is a linker linking the nucleobases through the attachment sites. The linkers in a given oligomer compound may be the same or different from one another. X and Y are terminating groups of the polymer. And, n is an integer, equal to 1 or greater.

The nucleobases of the present invention are limited only by their ability to conduct hydrogen-bonding interactions with the complementary nucleotides in a base-pair specific manner and their possession of at least two sites for covalent linkage through the inter-nucleobase linker, L, and terminii groups, X and Y. Linkers connect at carbon and nitrogen at the attachment sites of the nucleobases. Nucleobases at the termini are connected to a linker at one site. In a preferred embodiment, the linker, L, is attached to a non-destabilizing site of the nucleobase, where a non-destabilizing site is defined as a site where the attachment of a substituent group will not cause significant interference with either the hybridization of the nucleobase oligomer to its complementary strand in a duplex, or with the binding of the linker, L, to a nucleobase of a termini group, X or Y. Such non-destabilizing sites are found at C-8, C-7-deaza, and N-9 positions of purines and purine-analogs, and at C-5, C-6, and N-1 positions of pyrimidines and pyrimidine-analogs (Bergstrom, D. "C-5-Substituted Nucleoside Analogs" (1992) Synlett. March, 179–88).

In a preferred embodiment, B is 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6diamino-7-deaza purine, 5-methyl-cytosine, 5-propynyl-uridine, 5-propynyl-cytidine, 2-thio-thymine or 2-thio-uridine (FIGS. 2 and 3).

Figure 8:
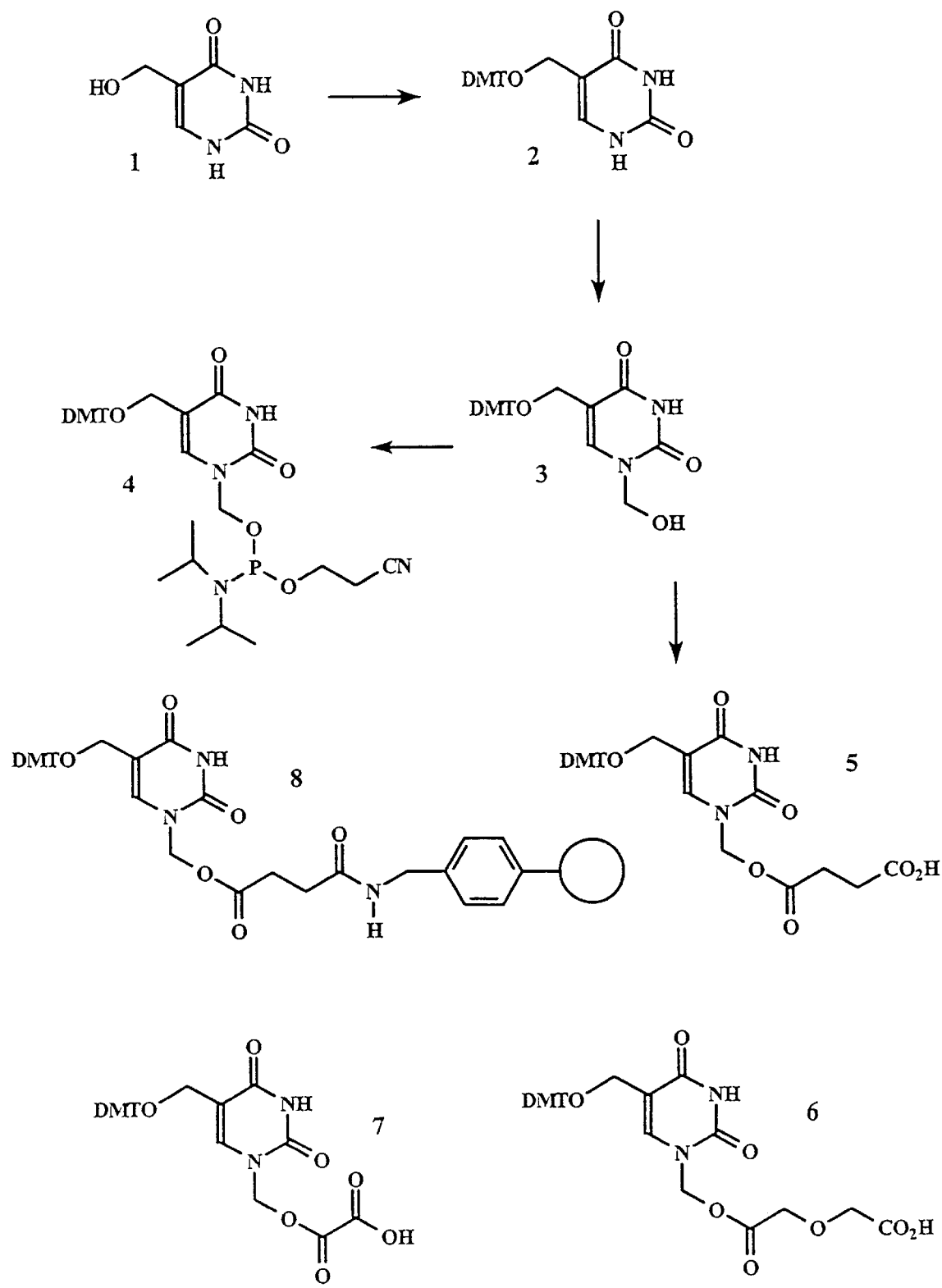
FIG. 8 Synthesis of reagents for nucleobase oligomer with phosphodiester bis-methyl linkages.
Figure 9:
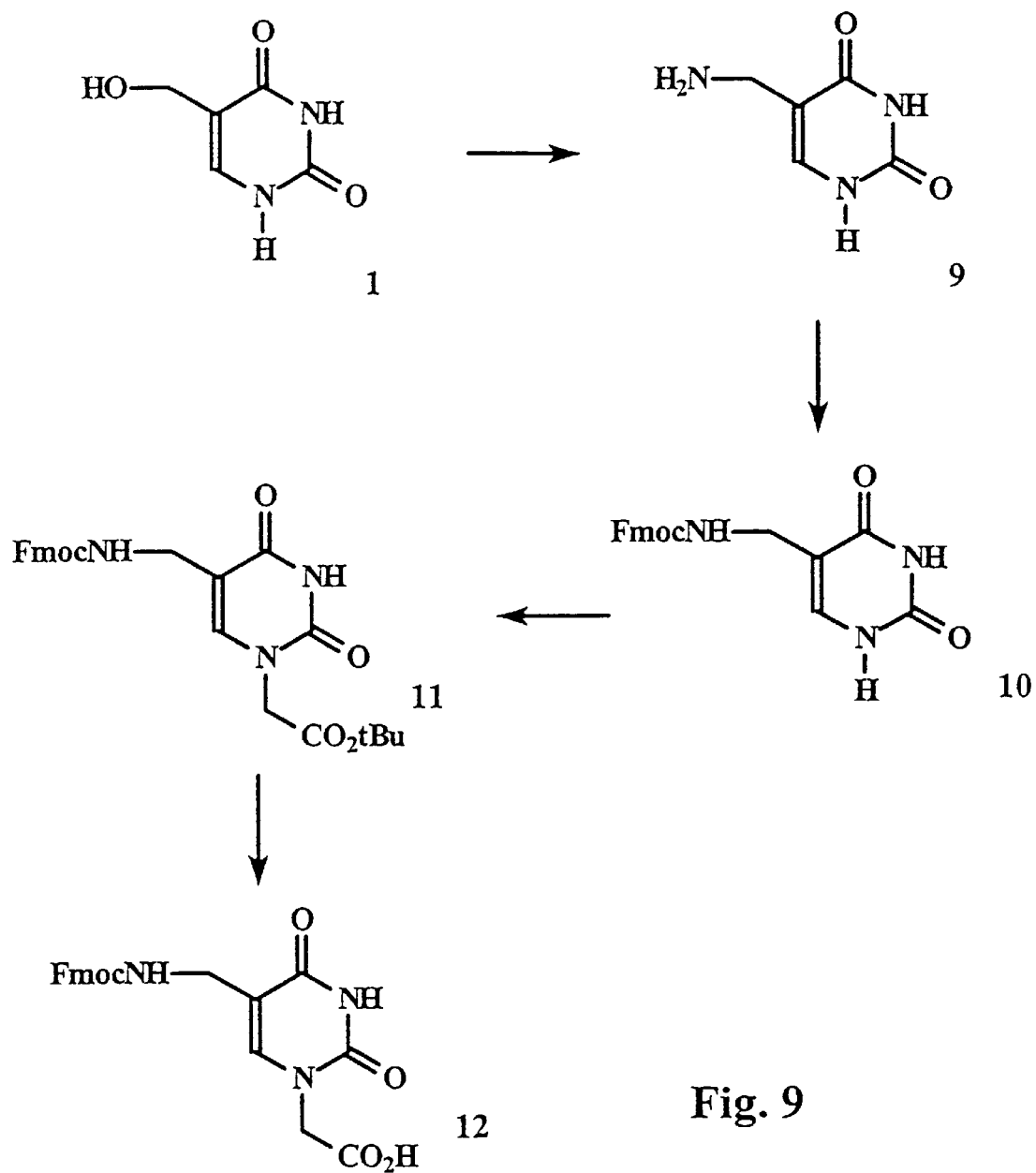
FIG. 9 Synthesis of reagents for nucleobase oligomer with amide methyl, ethyl linkages.
Figure 10:
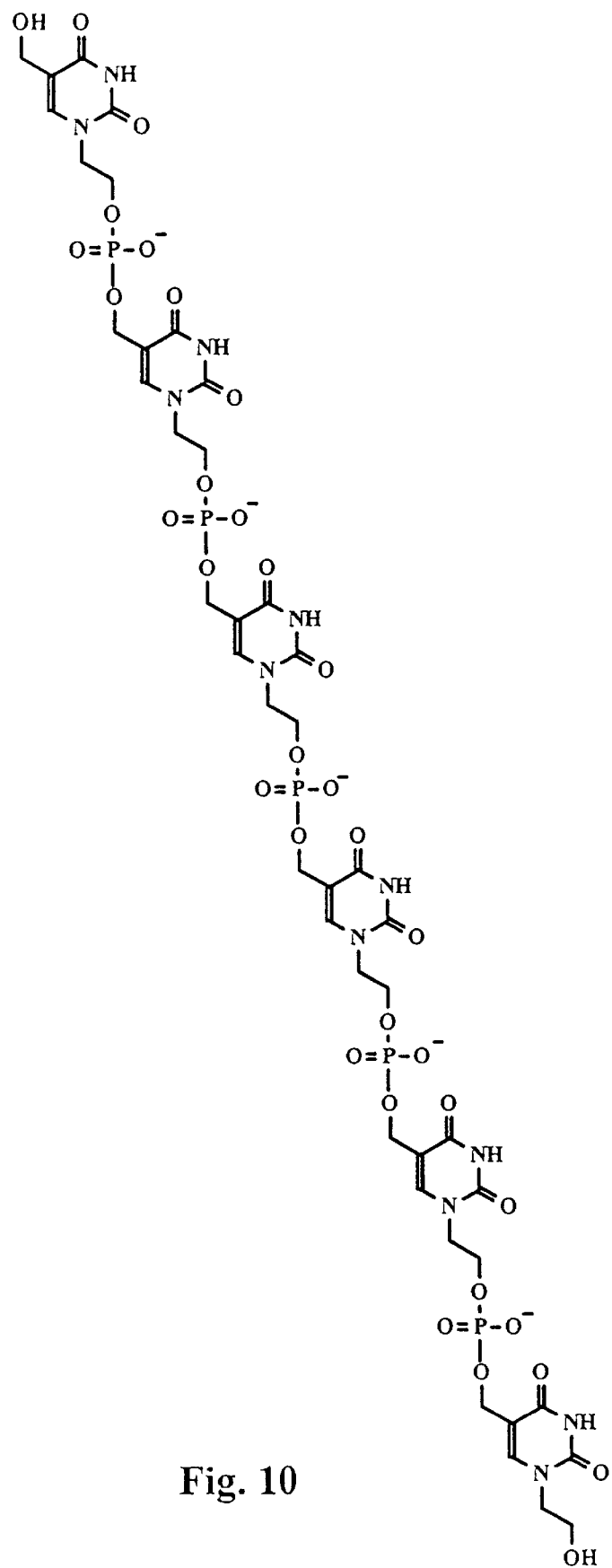
FIG. 10 Poly uracil nucleobase hexamer oligomer with phosphodiester methyl, ethyl linkages.
Figure 11:
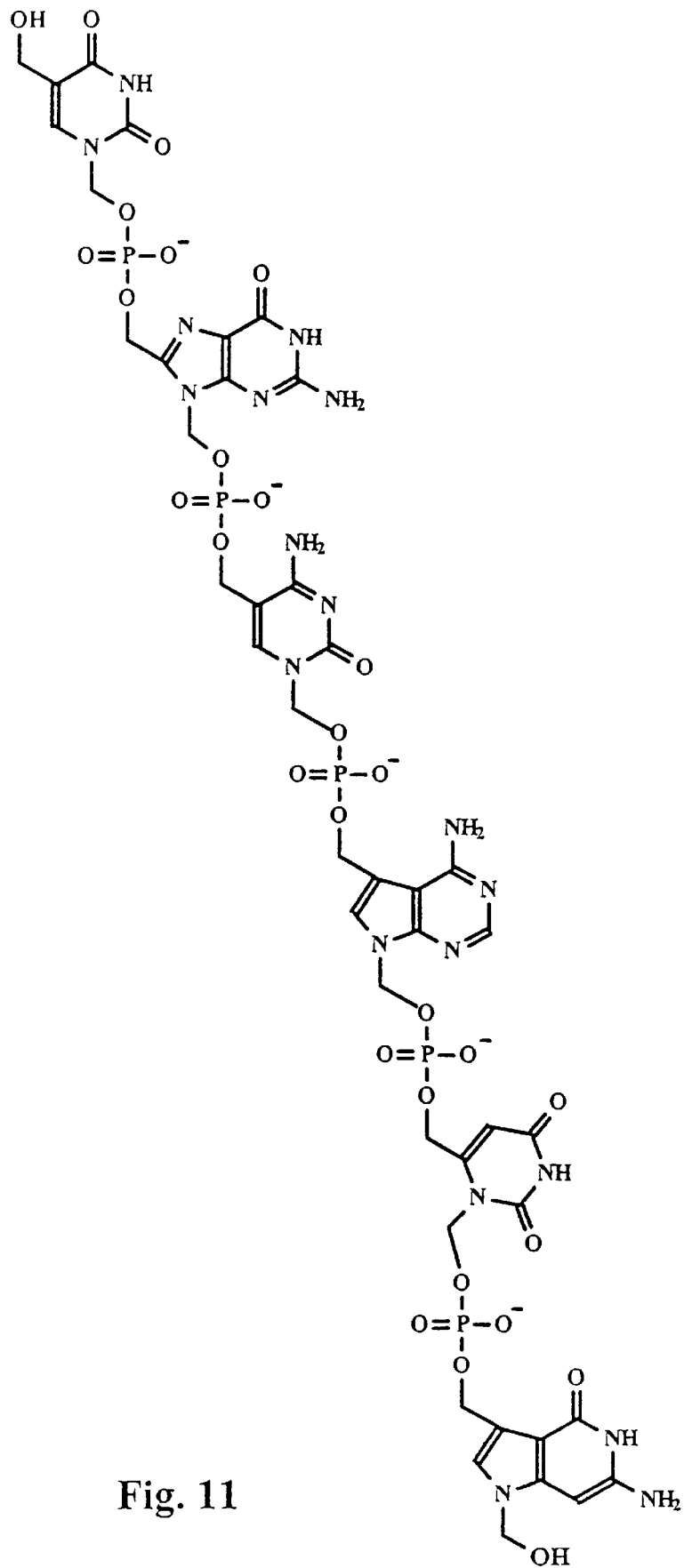
FIG. 11 Heterosequence, nucleobase oligomer with phosphodiester bis-methyl linkages.
Figure 12:
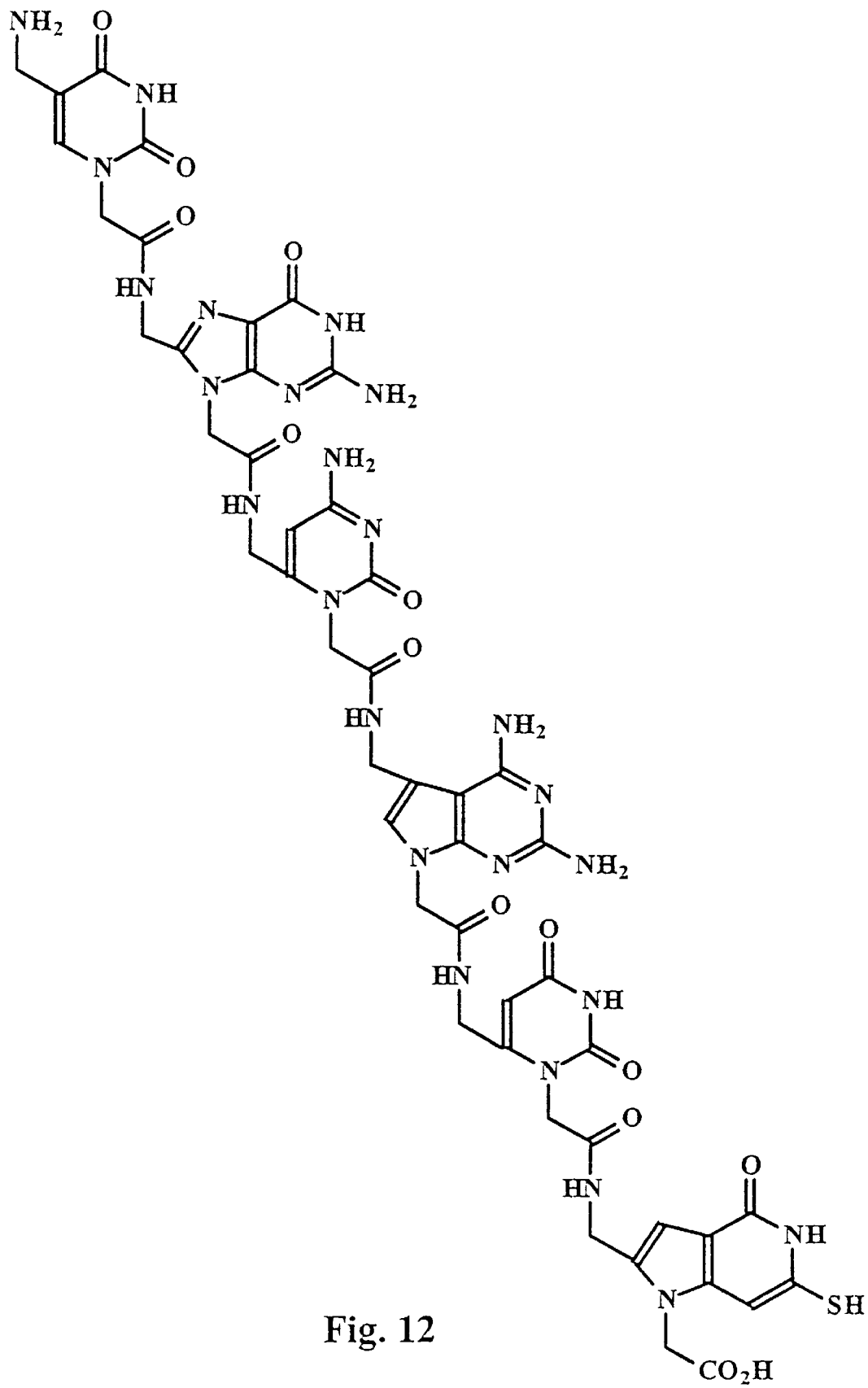
FIG. 12 Heterosequence, nucleobase oligomer with amide bis-methyl linkages.
Figure 13:
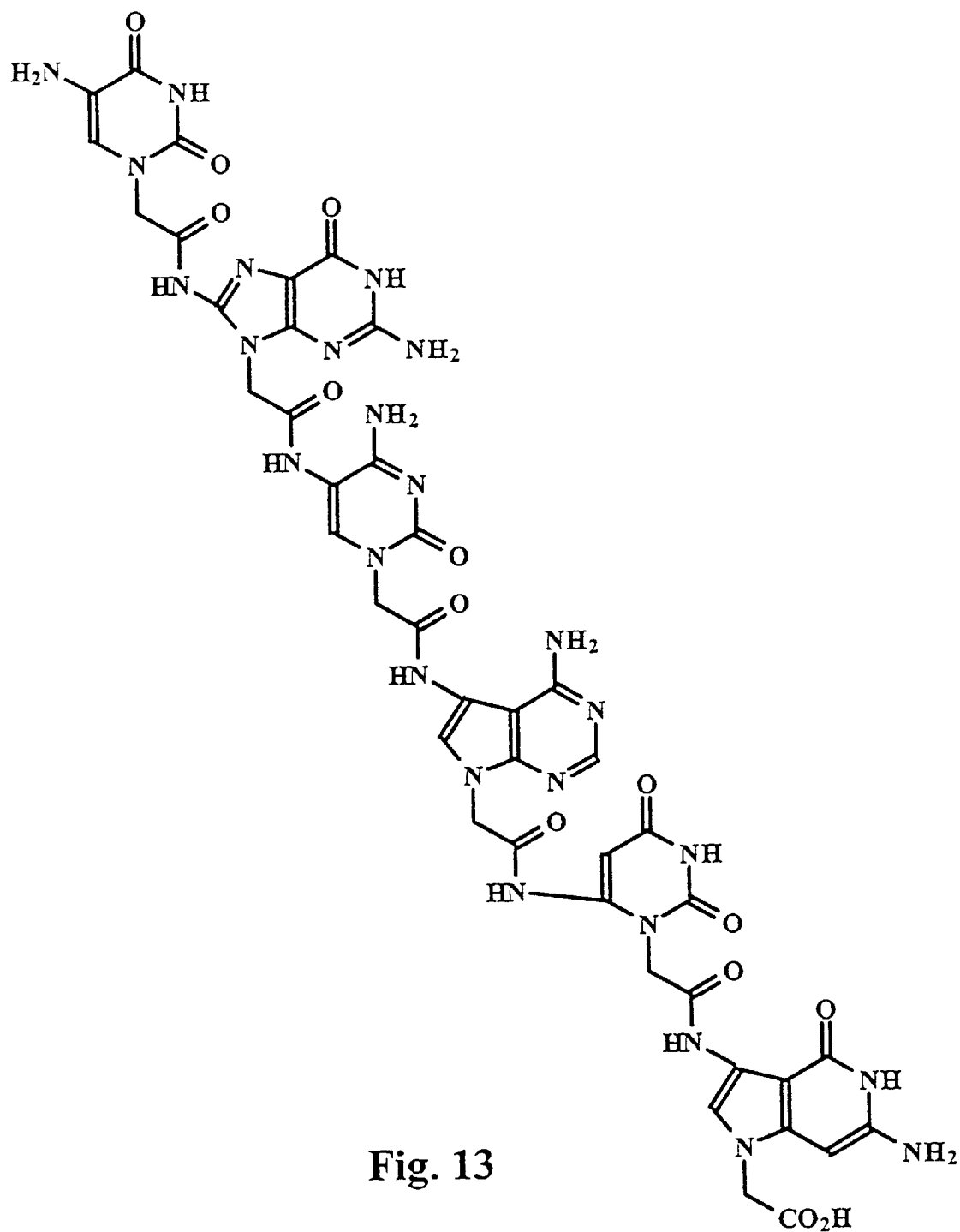
FIG. 13 Heterosequence, nucleobase oligomer with amide methyl linkages.

Linkers, L, serve to attach the nucleobase monomers together to form the nucleobase oligomer. They are comprised of functionality that enables efficient and low-cost synthesis of the oligomer compounds and monomeric units, e.g. 4 (FIG. 8) and 12 (FIG. 9). The present invention allows the use of a large variety of linker constructions. Preferred linkers are comprised of functionalities that enable efficient, automated, high-yield coupling reactions in the synthesis of nucleobase oligomers. The linkers may be used to confer nuclease resistance. The linkers determine the preferred conformation of the nucleobases, affecting affinity and specificity of base-pairing in hybridization. Examples of nucleobase oligomers with phosphodiester linkages are shown in FIGS. 10 and 11. Examples of nucleobase oligomers with neutral amide linkers are shown in FIGS. 12 and 13.

In another preferred embodiment, L is methylene, alkylene, substituted alkylene, substituted aryl, phosphodiester, phosphotriester, alkylphosphonate, phosphoramidate, phosphorothioate, disulfide, amide, ester, carbonyl, sulfonamide, carbamate, urea, ethyleneoxy, reactive functionality, detection labels, or capture labels.

The terminating groups X and Y serve a variety of purposes including; optimizing base-pairing properties, optimizing net hydrophobicity/hydrophilicity, and bearing a reactive functionality for covalent attachment to other groups. Groups attached at X and Y include labels for detection and capture of the nucleobase oligomer. The present invention allows for the use of a large variety of terminating groups (Hermanson, G. "Bioconjugate Techniques" (1996) Academic Press, San Diego, pp. 40–56).

In a third preferred embodiment, X and Y are independently hydrogen, mono-substituted alkyl, di-substituted alkyl, methylene, mono-substituted methylene, alkylene, mono-substituted alkylene, aryl, substituted aryl, reactive functionality, detection labels, capture labels, DNA, RNA, or nucleic acid analogs. Furthermore, L,X,Y may or may not be substituted with groups that enhance the base-pairing properties of the nucleobase oligomers.

In a second aspect, the invention relates to nucleobase monomer compounds having the structure:

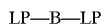

wherein B is a nucleobase as described in the nucleobase oligomers (FIGS. 2 and 3), and bearing a linker precursor, LP, at each of two attachment sites. The attachment sites to B are at N-1 and either C-5 or C-6 of pyrimidines and analogs, and at N-9 and either C-8 or C-7-deaza of purines and analogs. Illustrations of examples of the nucleobase monomer compounds are shown in FIG. 1. A linker precursor, LP, is comprised of a reactive functionality capable of forming linkages.

A reactive functionality of the linker precursor may have the structure:

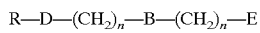

wherein R is an acid- or base-sensitive protecting group such as dimethoxytrityl, fluorenylmethyloxycarbonyl. D is oxygen, nitrogen, or sulfur. E is $CO_2H$ or a phosphoramidite moiety having the structure:

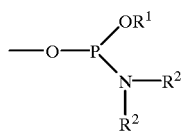

wherein $R^1$ may be a protecting group such as methyl or cyanoethyl. $R^2$ is a lower alkyl protecting group such as isopropyl. At least one methylene group attaches to the nucleobase, where n is an integer equal to 1 or greater. Examples of nucleobase monomer compounds are 4 (FIG. 8) and 12 (FIG. 9). Nucleobase monomers may be useful in the synthesis of nucleobase oligomers where E of one nucleobase monomer is activated to a reactive electrophile with a coupling reagent and forms a new bond with a nucleophile D of a second nucleobase monomer. The linker precursors, LP, of the first and second nucleobase monomers form the linker, L, of a nucleobase oligomer.

An advantage of the present invention is the reduction or elimination of non-Watson/Crick base pairing. Nucleic acids and analogs may possess intermolecular and intramolecular interactions which are non-Watson/Crick base pair specific (A+T, G+C). These interactions can cause destabilizing mismatches (e.g. G and T) in duplexes during primer and probe experiments. The presence of the linker at the attachment sites of the pyrimidine and purine nucleobases will prevent, disrupt, or minimize non-Watson/Crick hydrogen-bonding such as Hoogsteen base-pairing, involving the N-7 site of purines (Saenger, W. "Principles of Nucleic Acid Structure" (1984) Springer-Verlag, New York, pp. 116–58). Higher affinity and/or specificity may be achieved by the use of C-5 propynyl nucleobase analogs (Froehler, B. *Tetrahedron Letters* (1992) 33:5307–10). Other nucleobase analogs, such as isoguanine and 7-deaza-isoguanine may also be used to improve properties such as affinity and specificity of hybridization to complementary nucleic acids (Seela, F. *Helv. Chim. Acta* (1997) 80:73–85).

Affinity and specificity properties can be measured precisely and accurately by standard thermal melting experiments. Under controlled conditions, the nucleobase oligomer to be tested is mixed with its complementary nucleic acid and allowed to form its most stable conformation, typically a bimolecular, double helix duplex with hydrogen-bonding between each base pair (FIGS. 4–7). The mixture is placed in a temperature controlled cuvette in a spectrophotometer and the temperature of the cuvette is raised slowly. Continuous measurement of absorbance of UV light, typically about 260 nm, while heating will show a hyperchromic effect. As hydrogen bonds are broken upon heating, the net absorbance of the nuclebases increase. An inflection point, given by the first derivative of the resulting sigmoidal curve, is observed when absorbance is plotted versus temperature. When the duplex follows normal melting behavior, a two-state transition of duplex to single-stranded oligomers occurs. The inflection point corresponds to half of the oligomers in a duplex and half single-stranded. This temperature at this point is referred to as $T_m$ and provides for direct measurement of base-pairing properties, such as affinity and specificity. With appropriate controls, comparisons with other nucleic acids and analogs can be made and conclusions made concerning base-pairing properties (Blackburn, G. M. and Gait, M. J. Eds. "DNA and RNA structure" in *Nucleic Acids in Chemistry and Biology*, $2^{nd}$ Edition, (1996) Oxford University Press, p. 70–71; Breslauer, K. J., Frank, R., Blocker, H., and Marky, L. (1986) *Proc. Natl. Acad. Sci. USA*, 83:3746–50).

Nucleobase oligomers and chimera therof may be used in annealing reactions performed under conditions which are stringent enough to guarantee sequence specificity yet sufficiently permissive to allow formation of stable duplexes at an acceptable rate. The temperature and length of time required for annealing depend upon several factors including the base composition, length and concentration of the nucleic acid or analog strands, the nature of the solvent used, e.g., the concentration of cosolvents such as DMSO, formamide, or glycerol, and counter ions such as magnesium. Typically, hybridization (annealing) of oligonucleotides to template is carried out at a temperature that is approximately 5 to 10° C. below the estimated melting temperature of duplex in the annealing solvent. Under optimized conditions, the annealing reaction will be complete in a few seconds (Ausubel et al. eds., *Current Protocols* in *Molecular Biology Volume* 1, Chapter 2, (1993) John Wiley & Sons, New York).

Primer extension reactions play an important role in several important molecular biology methods, e.g., annealing of primers to target nucleic acid sequences to probe for the presence or absence of genes, polynucleotide sequencing, and polynucleotide amplification. Nucleobase oligomers of the invention may be used as primers in various primer extension procedures. In conventional template-mediated primer extension reaction, an oligonucleotide primer having Watson/Crick base-pair complementarity to a single-stranded template nucleic acid is caused to anneal and then provided with a DNA polymerase in the presence of nucleoside triphosphates under conditions in which the DNA polymerase extends the 3' termini of the primer to form a complementary strand to the template nucleic acid.

Nucleobase oligomers of the invention and chimera therof may be used as primers in primer extension reactions, e.g. polynucleotide sequencing experiments. In a Sanger-type DNA sequencing reaction, the primer is extended by a DNA polymerase in the presence of a chain-terminating agent, e.g., a 2',3'-dideoxynucleoside triphosphate, to cause base-specific termination of the primer extension (Sanger et al., *Proc. Nat'l. Acad. Sci.,* (1977) 74: 5463–67).

Nucleobase oligomer chimera therof may also be used as primers in amplification reactions e.g. using the polymerase chain reaction (PCR) (Mullis, U.S. Pat. Nos. 4,683,195, 4,683,195, and 4,683,202). Generally, the PCR consists of an initial denaturation step which separates the strands of a double stranded target nucleic acid sample, followed by the repetition of: 1. an annealing step, which allows amplification primers to anneal specifically to opposite strands of the target and at positions flanking a target sequence; 2. an extension step which extends the primers in a 5'→3' direction thereby forming a complementary copy of the target, and; 3. a denaturation step which causes the separation of the copy and the target. Each of the above steps may be conducted at a different temperature, where the temperature changes may be accomplished using a thermocycler apparatus. Repetition of steps 1–3 by simple temperature cycling of the sample results in an exponential phase of replication, typically generating a million copies of the target duplex in 20–40 cycles (Innis et al., *PCR Protocols: A Guide to Methods and Applications,* (1990) Academic Press, Saiki et al., *Science,* (1988) 239: 487).

GENERAL SYNTHETIC METHOD

Nucleobase oligomers and chimeras thereof are preferably prepared from monomeric units by solid-support, automated synthesis. Each reactive monomer is added sequentially to the reactive termini of the growing chain while the opposite termini is covalently bound to a solid-phase bead or material. The bond formed in the coupling reaction of oligomer synthesis forms between reactive functionalities on the linkers of the growing chain and the monomer. The monomer and oligomer synthesis methods, including, reaction conditions, protocols, reagents, solid-support, and protecting groups depend on the linker.

Monomers for use in the preparation of nucleobase oligomers may be prepared as follows. Monomer unit 1can be prepared from 5-hydroxymethyl uridine 2 (FIG. 8). Reaction of 2 with 4,4'-dimethoxytrityl chloride in the presence of base gives the C-5-O-dimethoxytrityl intermediate 3 as the major product. Treatment of 3 with paraformaldehyde will form N-1 hydroxymethyl intermediate 4. Alternatively, hydroxymethylation can be carried out with known alkylating reagents, for example, benzyloxymethyl chloride, followed by hydrogenative removal of benzyl with palladium catalysis, or 2-trimethylsilylethyl chloride (SEM-Cl), followed by desilylation with tetrabutylammonium fluoride in tetrahydrofuran. Alternatively, hydroxymethylation can be carried out with other known acylating reagents, followed by reduction, for example, formylation with ethyl formate and reduction with sodium borohydride. Conversion of 4 to the phosphoramidite monomer unit 1 can be conducted with a phosphitylating reagent, e.g. bis-diisopropylamine-cyanoethoxyphosphine, and a catalyst, diisopropylammonium-1-H tetrazolide.

The support-bound nucleobase may be synthesized by succinylation of 4 with succinic anhydride to give the acid/ester 5. Alternatively, a more hydrolytically labile linker may be used. Reaction of 4 with diglycolic anhydride or oxalyl chloride will give the acid/esters 6 and 7, respectively. Coupling of 5 to aminomethyl, high cross link, polystyrene yields the nucleobase solid-support 8, ready for automated synthesis of a phosphate-linked nucleobase oligomer.

In another embodiment of the present invention, to prepare the monomers for nucleobase oligomer synthesis with an amide linkage group, 5-hydroxymethyl uracil 1 is converted to 5-aminomethyl uracil 9 (FIG. 9). Reaction of 1 with p-toluenesulfonyl chloride gives the 5-p-toluenesulfonate ester, followed by displacement by sodium azide to 5-azidomethyl uracil, and reduction by triphenylphosphine to give 9. Protection of amine as the Fmoc derivative 10 proceeds with 9-fluorenylmethylchloroformate in diisopropylethylamine and dimethylformamide. Alternatively, the amine of 9 can be protected with ethyl trifluoroacetate to give the trifluoroacetyl protected 10. Alkylation of 10 with tert-butyl bromoacetate in potassium carbonate and methanol gives ester 11. Saponification of the ester gives 12, the monomer for amide-linked, nucleobase oligomers.

Generally, the nucleobase oligomers and chimeras thereof may be synthesized using known synthetic techniques. Detailed descriptions of the chemistry used to form oligonucleotides are provided elsewhere (PE Applied Biosystems, Users Manual Model 392 and 394 DNA/RNA Synthesizers). The phosphoramidite method of oligonucleotide synthesis for making the phosphodiester nucleobase oligomers and chimeras thereof of the invention is the preferred method because of its efficient and rapid coupling and the stability of the starting materials (Beaucage, S. L. and Iyer, R. P. "Advances in the synthesis of oligonucleotides by the phosphoramidite approach" *Tetrahedron* (1992) 48:2223–2311, "The functionalization of oligonucleotides via phosphoramidite derivatives" *Tetrahedron* (1993) 49:1925–63, "The synthesis of modified oligonucleotides by the phosphoramidite approach and their applications" *Tetrahedron* (1993) 49:6123–94, "The synthesis of specific ribonucleotides and unrelated phosphorylated biomolecules by the phosphoramidite method" *Tetrahedron* (1993) 10441–88). The synthesis is performed with the growing oligomer chain attached to a solid support, so that excess reagents, which are in the liquid phase, can be easily removed by filtration, thereby eliminating the need for purification steps between cycles.

The following briefly describes the steps of a cycle for synthesizing the nucleobase oligomers of the invention using the phosphoramidite method. First, a solid-support, bearing a nucleobase, for example 8, bound at the 3' to the solid-support, is treated with acid, e.g., trichloroacetic acid, to remove a hydroxyl protecting group, e.g., dimethoxytityl group, from the 5' hydroxyl. The coupling reaction is then initiated by delivering an activated intermediate, formed by simultaneously adding a protected phosphoramidite nucleobase, for example 4, and a weak acid, e.g., tetrazole, and the like, to the solid-support. The nucleophilic 5' hydroxyl at the termini of the growing nucleobase oligomer chain displaces the tetrazolyl or protonated amine group at phosphorus of the monomer, which is present in excess. Next, a capping step is performed which terminates any nucleobase oligomer chains that did not undergo coupling. Capping is preferably done with acetic anhydride and 1-methylimidazole. The internucleobase linkage is then converted from trivalent phosphite to the desired, and more stable, phosphotriester by oxidation using iodine as the preferred oxidizing agent and water as the oxygen donor. Alternatively, oxidation can be conducted with a hydroperoxide reagent, such as tert.-butyl hydroperoxide. After oxidation, the hydroxyl protecting group is removed with a protic acid, e.g., trichloroacetic acid or dichloroacetic acid, in a step called detritylation, and the cycle is repeated until chain elongation is complete. After synthesis, the nucleobase oligomer chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases are removed by treating the nucleobase oligomer solution in base at an elevated temperature, e.g., 55° C. for 1–8 h. Examples of nucleobase oligomers are shown in FIGS. 10–13.

Figure 14:
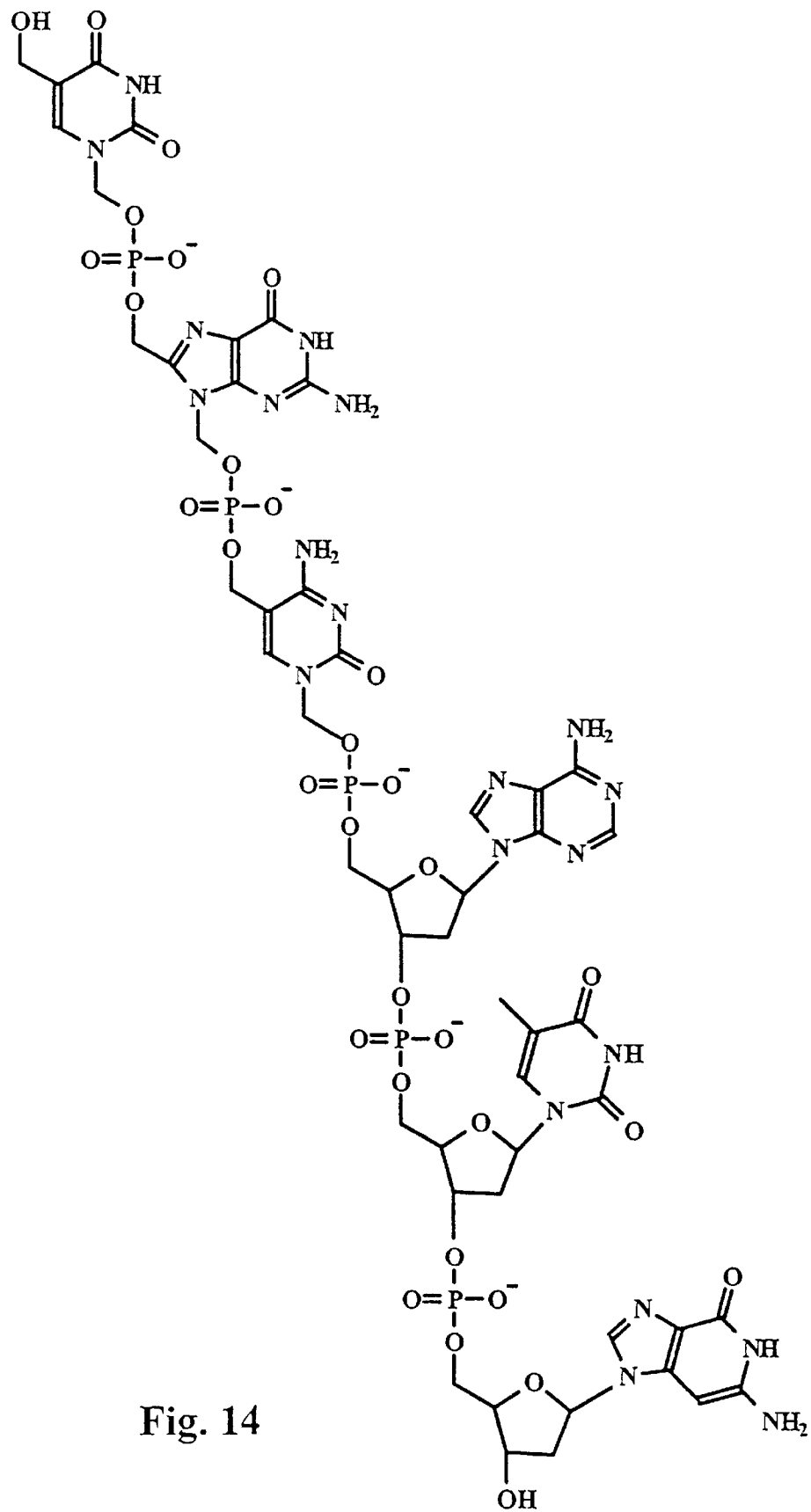
FIG. 14 Heterosequence, nucleobase/DNA chimera with phosphodiester linkages.
Figure 15:
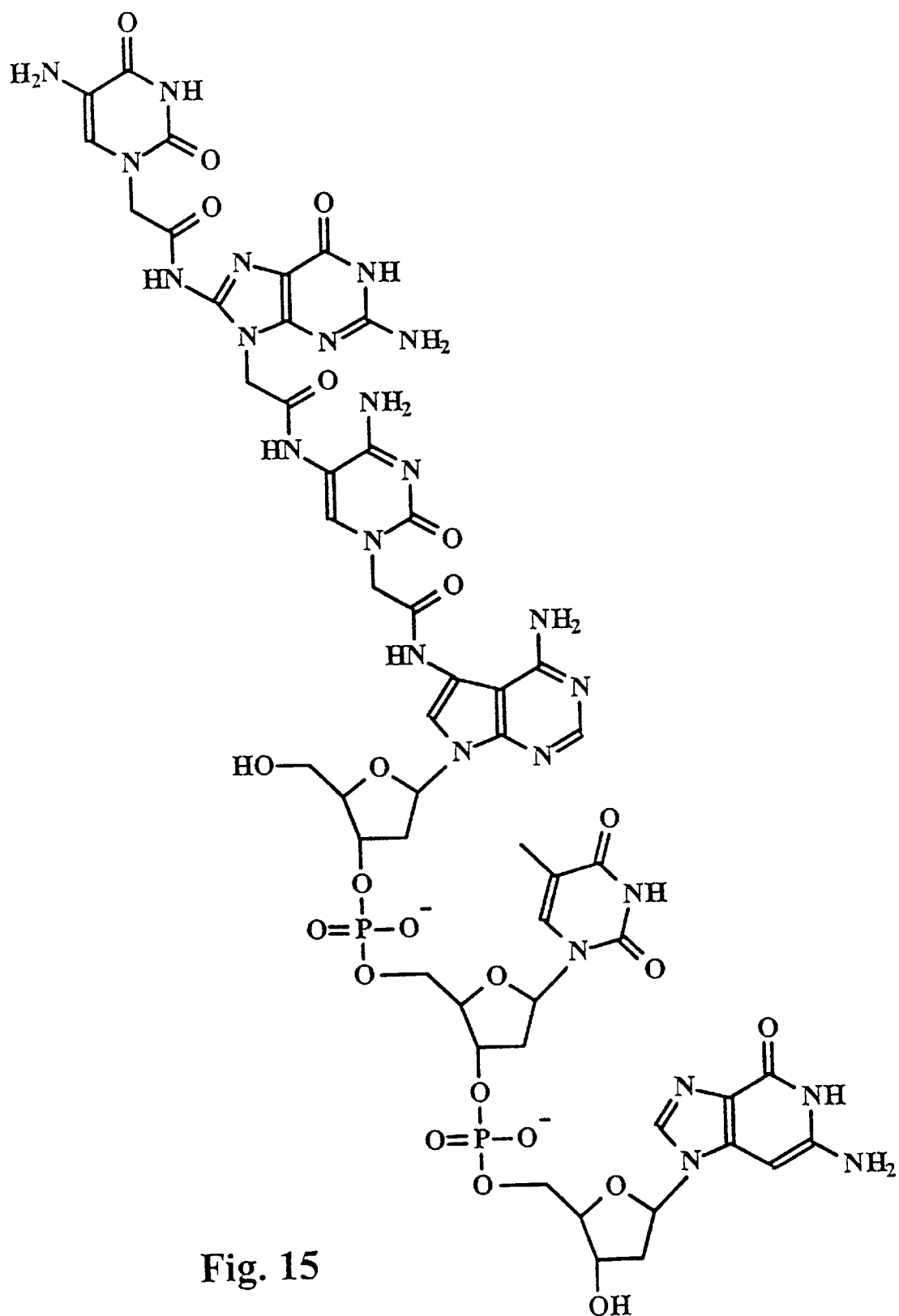
FIG. 15 Heterosequence, nucleobase/DNA chimera with amide and phosphodiester linkages.

Nucleobase oligomers and chimera therof may be synthesized on an ABI 394 DNA/RNA synthesizer or ABI 433 Peptide synthesizer (PE Applied Biosystems, Foster City, Calif.). For example, nucleobase oligomer/nucleic acid chimeras are made with DNA nucleoside phosphoramidites and RNA nucleoside phosphoramidites (PE Applied Biosystems, Foster City, Calif.) and 2'-OMe RNA nucleoside phosphoramidites (Glen Research, Sterling, Va.) phosphoramidite. The exocyclic amine nucleobase protecting groups are benzoyl (A and C) and dimethylformamide (G) for both the DNA and 2'-OMe RNA nucleosides. For each coupling cycle of the synthesis at the 1 μmole scale, 100 μl of 0.1 M monomer (ca. 10 mg) in acetonitrile is delivered concurrently with 320 μl of 0.5 M 5-H tetrazole in acetonitrile. Coupling times are 25 seconds for DNA nucleosides and 4 minutes for nucleobase monomers, 2'-OMe RNA nucleosides, PEO, and other analog and non-nucleosidic monomers. Examples of nucleobase olimer/nucleic acid chimeras are shown in FIGS. 14 and 15.

Synthesis efficiency may be followed during the synthesis in real-time by measuring the detritylation effluent from the reaction column with a trityl conductivity monitor. Average stepwise yields are generally greater than 98%. The 1 μmole scale gave about 100 crude odu (ca. 4 mg) odu (odu= absorbance at 260 nm of 1 mL volume in a 1 cm pathlength cell) of chimera. The nucleobase protecting groups are selected for comparable deprotection rates in concentrated ammonium hydroxide (1 hour at 65° C.) to minimize degradation or modification of the chimera oligonucleotide.

The conventional methods of nucleic acid analysis and purification, High Performance Liquid Chromatography (HPLC) and slab polyacrylamide gel electrophoresis (PAGE) with 7 M urea are the preferred methods for analysis and purification of nucleobase oligomers and chimeras thereof. PAGE purification typically yields 100 μg of product isolated from an electrophoresis run after loading 10–20 crude odu on a 3 mm thick gel, electrophoresing under standard conditions, excising the band after visualization under UV light against a TLC plate (EM Science, part # 5735), soaking in water overnight at room temperature, and desalting/concentrating on an Oligonucleotide Purification Cartridge (PE Applied Biosystems, part # 400771). Anion-exchange HPLC on a polymeric adsorbent (Dionex NucleoPac PA-100; 4×250 mm, Dionex Corporation) gives good resolution, predictable elution patterns, and reproducible retention times in nucleobase oligomer and chimera analysis and purification. A typical protocol is: mobile phase A—100 mM NaCl, 10 mM NaOH in 10% acetonitrile (pH 12); mobile phase B—800 mM NaCl, 10 mM NaOH in 10% acetonitrile (pH 12); elution flow rate—1.0 mL/min; linear gradient—0% B at 0 min to 80% B at 25 min.

EXAMPLES

The following examples are largely prophetic and intended to illustrate the preparation and application of the nucleobase oligomers of the present invention. The compounds shown and the values of the parameters used are only intended to exemplify the invention and are not to be considered limitations thereof.

Example 1

Synthesis of 5-(4,4'-dimethoxytrityloxymethyl)-uracil 2

5-(Hydroxymethyl)-uracil hydrate 1 (10.00 gm, 0.070 moles) is co-evaporated three times with 50 ml dry pyridine and dissolved in 200 ml dry pyridine at room temperature. Triethylamine (9.8 ml, 0.070 moles) and 4,4'-dimethoxytrityl chloride (23.7 gm, 0.070 moles) are added and the mixture is stirred for 6 hours under a nitrogen atmosphere. Most of the pyridine is removed under reduced pressure and the residue is partitioned between ethyl acetate and saturated sodium bicarbonate. The organic phase is washed twice with saturated sodium chloride, dried over magnesium sulfate, filtered, and evaporated under reduced pressure. The oily residue is triturated with ethyl acetate and hexane to give 5-(4,4'-dimethoxytrityloxymethyl)-uracil 2 as an off-white solid.

Example 2

Synthesis of N-1-(hydroxymethyl), 5-(4,4'-dimethoxytrityloxymethyl)-uracil 3

5-(4,4'-dimethoxytrityloxymethyl)-uracil 2 (15.00 gm, 0.034 moles) is dissolved in 200 ml dry tetrahydrofuran and 20 ml diisopropylethylamine at 0° C. under a nitrogen atmosphere. Paraformaldehyde (5.1 gm, 0.17 moles) is added in one portion. The ice water bath was removed and the mixture was stirred for 18 hours. Most of the solvent was removed under reduced pressure and the residue is partitioned between ethyl acetate and saturated sodium bicarbonate. The organic phase is washed twice with saturated sodium chloride, dried over magnesium sulfate, filtered, and evaporated under reduced pressure. The oily residue is triturated with ethyl acetate and hexane to give N-1-(hydroxymethyl), 5-(4,4'-dimethoxytrityloxymethyl)-uracil 3 as an off-white solid.

Example 3

Synthesis of N-1-(2-cyanoethyl N,N-diisopropylphosphoramidite, oxymethyl), 5-O-(4,4'-dimethoxytrityloxymethyl)-uracil 4

N-1-(hydroxymethyl), 5-O-(4,4'-dimethoxytrityloxymethyl)-uracil 3 (12.00 gm, 0.025 moles) is dissolved in 250 ml dry dichloromethane under a nitrogen atmosphere. Diisopropylammonium, 1-H tetrazolide (1.28 gm, 0.007 moles) is dissolved, followed by the addition of bis-diisopropylamine, cyanoethoxyphosphine (9.23 gm, 0.031 moles). After stirring overnite, 17 ml of a mixture of dimethylformamide:glycerol/2:1 (v/v) is added.

After one hour, the mixture is diluted with dichloromethane and washed successively with saturated sodium bicarbonate twice, water twice, and saturated sodium chloride. The organic phase is dried over sodium sulfate, filtered, and dried under reduced pressure to give a solid, which is dissolved in a minimum of ethyl acetate and chilled by an ice bath. Several volumes of hexane are added to induce precipitation. The white solid, N-1-(2-cyanoethyl N,N-diisopropyl-phosphoramidite, oxymethyl), 5-O-(4,4'-dimethoxytrityloxymethyl)-uracil 4, is collected by filtration and dried under vacuum.

Example 4

Synthesis of N-1-(Oxymethylsuccinic acid), 5-O-(4,4'-dimethoxytrityloxymethyl)-uracil 5

N-1-(hydroxymethyl), 5-(4,4'-dimethoxytrityloxymethyl)-uracil 3 (1.50 gm, 0.0034 moles), succinic anhydride (0.42 gm, 0.0042 moles), 4-dimethylaminopyridine (0.20 gm, 0.0017 moles), and 10 ml of dry pyridine are stirred for 16 hours at room temperature under a nitrogen atmosphere. The mixture is diluted with ethyl acetate and washed twice with 5% citric acid and saturated sodium chloride. The organic phase is dried over magnesium sulfate, filtered, and evaporated under reduced pressure. The residue is triturated by dissolution in a small volume of warm ethyl acetate followed by the addition of several volumes of hexane. The product, N-1-(oxymethylsuccinic acid), 5-O-(4,4'-dimethoxytrityloxymethyl)-uracil 5 is collected by filtration as an off-white solid.

Example 5

Synthesis of Solid-support, Polystyrene-N-1-(oxymethylsuccinamide methyl), 5-O-(4,4'-dimethoxytrityloxymethyl)-uracil 8

N-1-(oxymethylsuccinic acid), 5-O-(4,4'-dimethoxytrityloxymethyl)-uracil 5 (1.0 gm, 0.0017 moles) is dissolved in 8 ml dry dioxane and 0.5 ml dry pyridine under a nitrogen atmosphere at room temperature. 4-Nitrophenol (0.24 gm, 0.0017 moles) and 1,3-dicyclohexylcarbodiimide (0.88 gm, 0.0043 moles) are added and stirred for 5 hours under a nitrogen atmosphere. The fine precipitate of dicyclohexylurea is filtered and the filtrate is added to a suspension of 1000 angstrom pore, 50–70 micron diameter, high crosslinked, aminomethylpolystyrene (25 micromole amino/gm, 5.0 gm) in 5 ml dimethylformamdide and 1 ml triethylamine. The mixture is stoppered, and rocked with a wrist-action shaker for 16 hours at room temperature. The support is filtered, washed with methanol and diethylether, and dried under reduced pressure. The support is treated with a mixture of 20 ml pyridine, 2.5 ml acetic anhydride, and 2.5 ml N-methylimidazole. The mixture is stoppered, and rocked with a wrist-action shaker for 1 hour at room temperature. The support is filtered, washed with pyridine, methanol and diethylether, and dried under reduced pressure. Dimethoxytrityl analysis is conducted to determine the loading of 5-O-(4,4'-dimethoxytrityloxymethyl)-uracil on the polystyrene support. A small amount of the support is weighed accurately, placed in a volumetric flask and diluted with a measured amount of 0.1 molar p-toluenesulfonic acid in acetonitrile and agitated for several minutes. The absorbance of the orange solution at 490 nm in a 1 cm path length cuvette and assuming an extinction coefficient of 70,000 will calculate by Beer's law, the dimethoxytrityl cation released from polystyrene-N-1-(oxymethylsuccinamide methyl), 5-O-(4,4'-dimethoxytrityloxymethyl)-uracil 8 to be approximately 20 micromole/gm.

Example 6

Synthesis of Poly-(N-1, C-5 phosphodiester bis-methyl)-uracil by Automated Solid-phase Synthesis
(5') UUU UUU UUU UUU UUU U (3')

Figure 16:
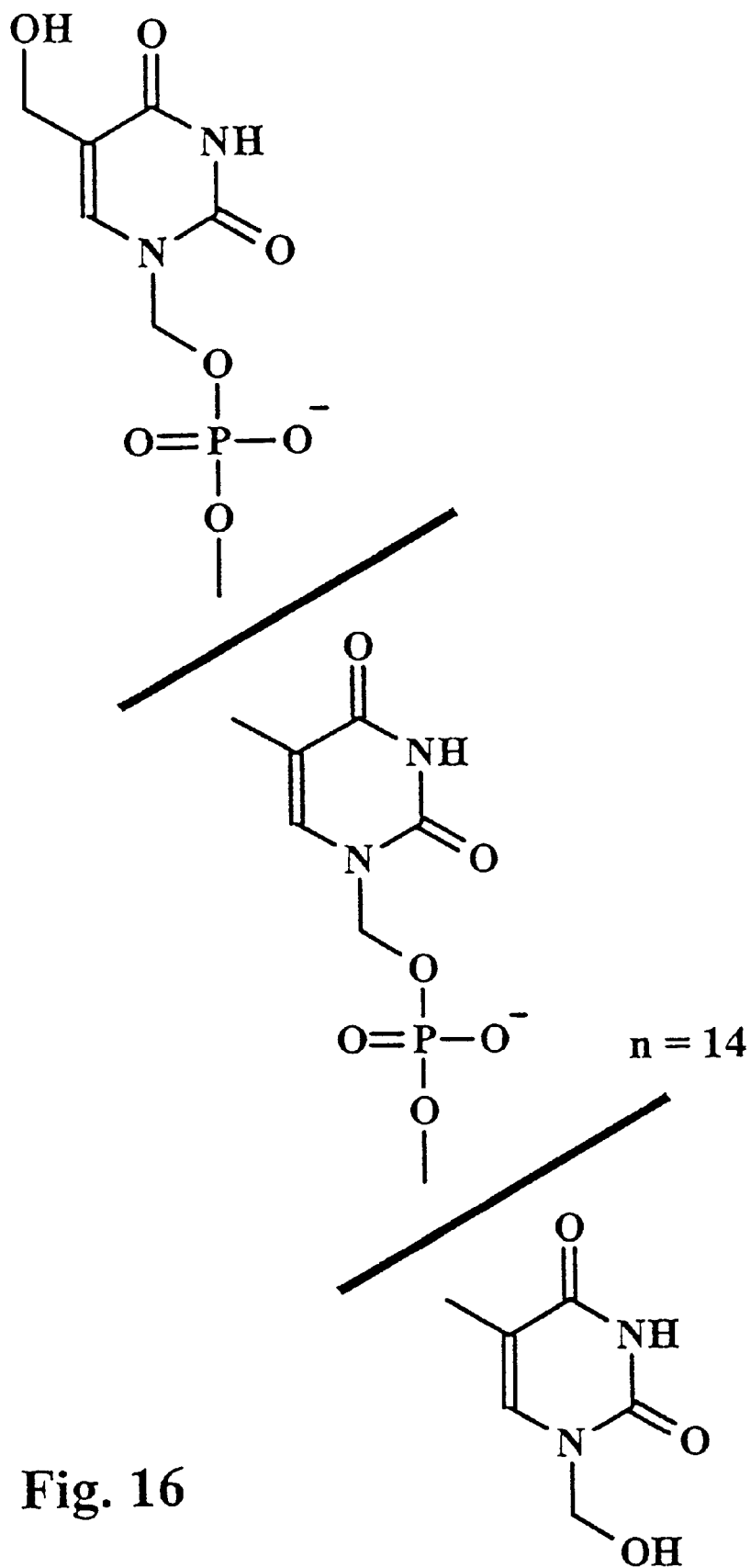
FIG. 16 Poly uracil nucleobase 16 mer oligomer with phosphodiester bis-methyl linkages.

Polystyrene-N-1-(oxymethylsuccinamide methyl), 5-O-(4,4'-dimethoxytrityloxymethyl)-uracil 8 (50 mg, 1 micromole, 20 micromoles/gm) is packed into a synthesis column, retained by frits, and mounted on an Applied Biosystems Model 394 Synthesizer. Normal reagents for the phosphoramidite chemistry method conducted by automated synthesis are employed, except for the monomer, N-1-(2-cyanoethyl N,N-diisopropyl-phosphoramidite, oxymethyl), 5-O-(4,4'-dimethoxytrityloxymethyl)uracil 4, which is used as a 0.1 M solution in dry acetonitrile. Approximately 10 mg of monomer 4 is used for each coupling reaction, which requires a time of 240 seconds for completion. After fifteen cycles of coupling, capping, oxidation, and detritylation reactions, the sixteen-mer, poly uracil nucleobase oligomer is complete. The dimethoxytrityl group is left intact at the terminus to facilitate HPLC purification. The support is dried under argon on the Model 394 Synthesizer where cleavage of the ester linkage to the polystyrene and deprotection of the cyanoethyl phosphotriester linkages are conducted with concentrated ammonium hydroxide for one hour at room temperature. The resultant ammonium hydroxide solution containing the crude oligomer is concentrated under vacuum, dissolved in 0.1 M triethylammonium acetate and purified by reverse-phase HPLC to give approximately 0.5–1 mg of purified dimethoxytrityl-$U_{16}$ nucleobase oligomer. The purified fraction is concentrated under vacuum and dissolved in 1 ml of a 4:1 mixture of acetic acid:water for 30 minutes at room temperature. 100 microliters of 3 M sodium acetate and 3 ml of isopropanol are added and mixed to cause precipitation of the product, purified $U_{16}$ nucleobase oligomer (FIG. 16), which is isolated by centrifugation and removal of the supernatant.

Example 7

Thermal Melting Study of Hybridization of Nucleobase Oligomers and Chimera with DNA Thermal UV melting experiments are performed on nucleobase oligomers and chimera with DNA to determine the intramolecular $T_m$ as a measure of hybridization. The nucleobase oligomers or chimeras, and complementary DNA are dissolved in the buffer at concentrations of about 1 micromolar and containing 10 mM HEPES, pH 7.3, and 25 mM NaCl. Absorbance at 260 nm is monitored as a function of temperature between 30–90° C. at a heating rate of 0.5° C. $\min^{-1}$. The $T_m$ studies are conducted using a Perkin-Elmer Lambda 12 spectrometer equipped with a PC-controlled Peltier heating unit.

Upon heating, a plot of absorbance versus temperature will show a sigmoidal shape, with a single, sharp transition consistent with a simple two-state model of duplex melting to independent strands. The maximum of the first derivative curve is the melting temperature, $T_m$, the value of which is a relative indicator of duplex stability, or affinity. Experiments with single-base mismatches in the nucleobase oligomer and chimeras, or in the DNA strands will yield information about specificity.

All papers and documents (including patents) referenced in this specification are incorporated herein by reference.

Although the present invention has been described in considerable detail with reference to certain preferred versions thereof, other versions are possible. Those skilled in the art of chemistry will understand that there are many variations of the above monomers and oligomers, and methods for their synthesis, that fall within the preview of the present invention.

What is claimed is:

1. A polymer compound consisting of the formula (Figure)

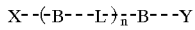

wherein:
(a) B is a nucleobase capable of effecting Watson/Crick base-pairing and bearing two linking attachment sites;
(b) L is a linker consisting of 4 to 7 bonds and linking two nucleobases through the linking attachment sites;
(c) X and Y are terminating groups; and
(d) n is an integer equal to 1 or greater.

2. The compound of claim 1 wherein the linking attachment sites are at
N-1 and either C-5 or C-6 of pyrimidines and at N-9 and either C-8 or C-7-deaza of purines.

3. The compound of claim 1 wherein
B is selected from the group consisting of 7-deaza-adenine, 7-deaza-guanine, adenine, guanine, cytosine, thymine, uracil, 2-deaza-2-thio-guanosine, 2-deaza-2-thio-7-deaza-guanosine, 2-thio-adenine, 2-thio-7-deaza-adenine, isoguanine, 7-deaza-isoguanine, 5,6-dihydro-uracil, 5,6-dihydro-thymine, xanthine, 5-amino-cytidine, 5-amino-uracil, 7-deaza-xanthine, hypoxanthine, 7-deaza-xanthine, 2,6-diamino-7-deaza purine, 5-methyl-cytosine, 5-bromo-uracil, 5-chloro-uracil, 5-fluoro-uracil, 5-propynyl-uracil, 5-propynyl-cytidine, 2-thio-thymine and 2-thio-uridine.

4. The compound of claim 3 wherein
B is selected from the group consisting of 7-deaza-adenine, 7-deaza-guanine, adenine, guanine, cytosine, thymine, and uracil.

5. The compound of claim 1 wherein
L is selected from the group consisting of methylene, lower alkylene, lower substituted alkylene, substituted aryl, phosphotriester, alkylphosphonate, phosphoramidate, phosphorothioate, disulfide, ester, carbonyl, sulfonamide, carbamate, urea, ethyleneoxy, and polyethyleneoxy.

6. The compound of claim 1 wherein
L is selected from the group consisting of phosphodiester and amide.

7. The compound of claim 1 wherein
at least one of X and Y are selected from the group consisting of hydrogen, mono-substituted lower alkyl, di-substituted lower alkyl, methylene, mono-substituted methylene, lower alkylene, mono-substituted lower alkylene, aryl, and substituted aryl.

8. The compound of claim 1 wherein
at least one of X and Y are labels.

9. The compound of claim 8 wherein
at least one of X and Y are labels selected from the group consisting of biotin, dinitrophenyl, acridine, fluorescein, and digoxigenin.

10. The compound of claim 8 wherein
at least one of X and Y are labels selected from the group consisting of fluorescein, rhodamine, and cyanine.

11. The compound of claim 8 wherein
at least one of X and Y are chemiluminescent precursors having the structure

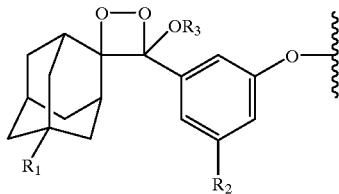

where $R_1$ is hydrogen or halogen; $R_2$ is phosphate, galactoside, glucoside, glucuronide, trialkylsilyloxy, acyloxy, or hydrogen; and $R_3$ is methyl, ethyl, or lower alkyl.

12. The compound of claim 1 wherein
at least one of X and Y are selected from the group consisting of —OH, —$NH_2$, —$CO_2H$, and —SH.

13. The compound of claim 1 wherein
at least one of X and Y are selected from the group consisting of DNA, RNA, and nucleic acid analogs terminating in a 5' or 3' hydroxyl group.

14. The compound of claim 13 wherein
the site of attachment of said nucleobase oligomer to said DNA, RNA, or nucleic acid analogs in a chimera occurs at a 5' or 3' hydroxyl of the DNA, RNA, or nucleic acid analogs.

15. The compound of claim 1 wherein L is selected from the group consisting of the structures

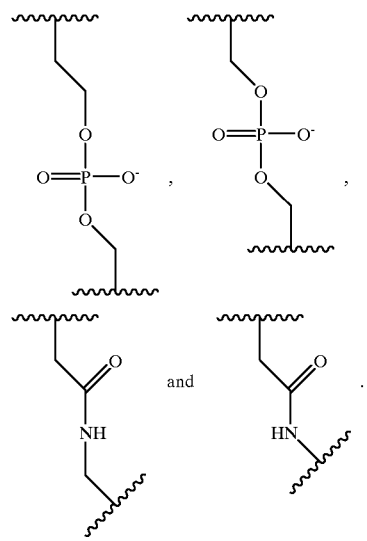

* * * * *